Figure 1:
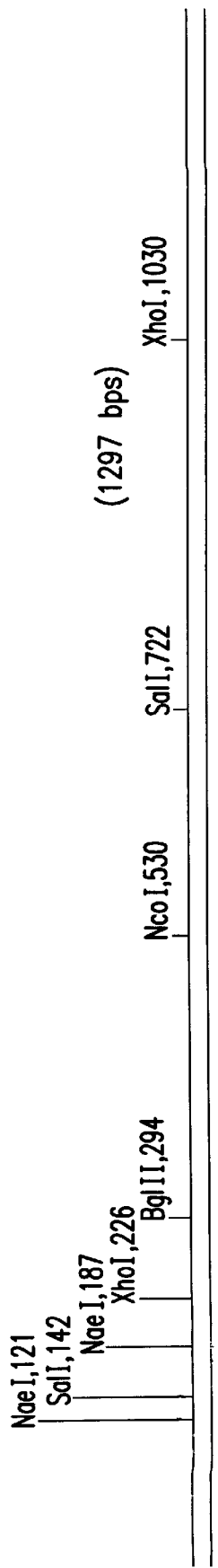

United States Patent [19]
Boudet et al.

[11] Patent Number: 6,015,943
[45] Date of Patent: Jan. 18, 2000

[54] DNA SEQUENCES CODING FOR A CINNAMOYL COA REDUCTASE AND THEIR USES IN THE FIELD OF REGULATING THE LIGNIN LEVELS OF PLANTS

[75] Inventors: Alain Boudet, Toulouse; Jacqueline Pettenati, Fourqueveaux; Deborah Goffner, Vieille Toulouse, all of France; Claire Halpin, Fife; Ann O'Connell, Weybridge, both of United Kingdom; Michel Romestant, Rodez, France; Wout Boerjan, Kalken, Belgium; Jean-Charles Leple, Ferolles, France

[73] Assignee: Centre National de la Recherche Scientifique, France

[21] Appl. No.: 08/722,184

[22] PCT Filed: Apr. 11, 1995

[86] PCT No.: PCT/FR95/00465

§ 371 Date: Feb. 24, 1997

§ 102(e) Date: Feb. 24, 1997

[87] PCT Pub. No.: WO95/27790

PCT Pub. Date: Oct. 19, 1995

[30] Foreign Application Priority Data

Apr. 11, 1994 [FR] France ................................... 94/04246

[51] Int. Cl.[7] ........................... C12N 15/00; C12N 15/29; C12N 15/82; A01H 4/00
[52] U.S. Cl. .......................... 800/298; 800/295; 800/278; 435/320.1; 435/419; 435/468; 536/24.1; 536/23.6
[58] Field of Search ..................... 800/202, 205, 800/250, 298, 295, 278; 536/24.1, 23.6; 435/172.3, 320.1, 419, 468

[56] References Cited

FOREIGN PATENT DOCUMENTS 0155872  9/1985  European Pat. Off. .
WO 93/05159  3/1993  WIPO ............................. C12N 15/53

OTHER PUBLICATIONS

J.Cell.Biochem. Suppl., vol. 17A, 1993, p. 26, M.M. Campbell, et al. "Hydroxycinnamoyl–coA reductase from Eucalyptus, Molecular analysis of a key control point of lignification", No. A305.

Theoretical and Applied Genetics, vol. 87, No. 8, Mar. 1994, pp. 1006–1015, T.R. Carron, et al., "Genetic Modification of Condensed Tannin Biosynthesis in Lotus Corniculatus.1. Heterologus Antisense Dihydroflavonol Reductase Down–Regulates Tannin Accumulation in 'Hairy Root'Cultures".

Bull. Liaison—Groupe Polyphenols, vol. 16 (Pt.2) 1992 pp. 295–300, M.P. Robbins et al. "Manipulation of Condensed Tannin Biosynthesis in Forage Legumes".

EMBL Accession No. T13840, Rel. 38, Mar. 7, 1994, 2005 Arabidopsis Thaliana CDNA Clone 41H9T7.

New Phytologist 129(2), 1995, pp. 203–236, A.M. Boudet, et al., "Tansley review No. 80; Biochemistry and molecular biology of lignification".

Biological Abstracts, vol. 78, 1984, Philadelphia, PA., Abst. No. 14461, F. SARNI, et al., Purification and properties of cinnamoyl–coenzyme A reductase (EC 1.2.1.44) and cinamyl alcohol dehydrogenase (EC 1.1.1.1) from poplar stems (populus euamericana).

Plant Physiology (1994), vol.106, pp. 625–632, Goffner, et al., "Purification and characterization of cinnamoyl–coenzyme A:NADP oxido–reductase in Ecalyptus gunnii".

Plant Molecular Biology, vol. 13, 1989, pp. 491–502, M. Beld, et al. "Flavonoid Synthesis in Petunia Hybrida: Partial Characterization of Dihydroflavonol–4–Reductase Genes".

French Research Report dated Dec. 16, 1994.

Sarni et al. Biological Abstracts vol. 78, 1984, abstract No. 14461, 1984.

*Primary Examiner*—Lynette R. F. Smith
*Assistant Examiner*—Thomas Haas
*Attorney, Agent, or Firm*—Bell, Boyd & LLoyd

[57] ABSTRACT

DNA sequences comprising, as coding region, all or part of the nucleotide sequence coding for an mRNA coding for a cinnamoyl CoA reductase (CCR), or all or part of the complementary nucleotide sequence thereof and coding for an anti-sense mRNA capable of hybridizing with the above-mentioned mRNA. The invention also concerns the use of said sequences for carrying out methods of regulation of plant lignin biosynthesis.

20 Claims, 5 Drawing Sheets

SEQUENCE LISTING (1) GENERAL INFORMATION:

(iii) NUMBER OF SEQUENCES: 10

(2) INFORMATION FOR SEQ ID NO:1:

(i) SEQUENCE CHARACTERISTICS:
        (A) LENGTH: 1297 base pairs
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (ix) FEATURE:
        (A) NAME/KEY: CDS
        (B) LOCATION: 136..1140

(xi) SEQUENCE DESCRIPTION: SEQ ID NO:1:

```
CGGCCGGGAC GACCCGTTCC TCTTCTTCCG GGTCACCGTC ACCATGTTAC ACAACATCTC      60

CGGCTAAAAA AAAAAGGAAA AAAAGCGCAA CCTCCACCTG CTGAACCCCT CTCCCCCCTC     120

GCCGGCAATC CCACC ATG CCC GTC GAC GCC CTC CCC GGT TCC GGC CAG ACC     171
                Met Pro Val Asp Ala Leu Pro Gly Ser Gly Gln Thr
                  1               5                  10

GTC TGC GTC ACC GGC GCC GGC GGG TTC ATC GCC TCC TGG ATT GTC AAG     219
Val Cys Val Thr Gly Ala Gly Gly Phe Ile Ala Ser Trp Ile Val Lys
        15                  20                  25

CTT CTC CTC GAG CGA GGC TAC ACC GTG CGA GGA ACC GTC AGG AAC CCA     267
Leu Leu Leu Glu Arg Gly Tyr Thr Val Arg Gly Thr Val Arg Asn Pro
 30                  35                  40

GAC GAC CCG AAG AAT GGT CAT CTG AGA GAT CTG GAA GGA GCC AGC GAG     315
Asp Asp Pro Lys Asn Gly His Leu Arg Asp Leu Glu Gly Ala Ser Glu
 45                  50                  55                  60

AGG CTG ACG CTG TAC AAG GGT GAT CTG ATG GAC TAC GGG AGC TTG GAA     363
Arg Leu Thr Leu Tyr Lys Gly Asp Leu Met Asp Tyr Gly Ser Leu Glu
                 65                  70                  75

GAA GCC ATC AAG GGG TGC GAC GGC GTC GTC CAC ACC GCC TCT CCG GTC     411
Glu Ala Ile Lys Gly Cys Asp Gly Val Val His Thr Ala Ser Pro Val
             80                  85                  90

ACC GAC GAT CCT GAG CAA ATG GTG GAG CCA GCG GTG ATC GGG ACG AAA     459
Thr Asp Asp Pro Glu Gln Met Val Glu Pro Ala Val Ile Gly Thr Lys
         95                 100                 105

AAT GTG ATC GTC GCA GCG GCG GAG GCC AAG GTC CGG CGG GTT GTG TTC     507
Asn Val Ile Val Ala Ala Ala Glu Ala Lys Val Arg Arg Val Val Phe
    110                 115                 120

ACC TCC TCC ATC GGT GCA GTC ACC ATG GAC CCC AAC CGG GCA GAC GTT     555
Thr Ser Ser Ile Gly Ala Val Thr Met Asp Pro Asn Arg Ala Asp Val
125                 130                 135                 140

GTG GTG GAC GAG TCT TGT TGG AGC GAC CTC GAA TTT TGC AAG AGC ACT     603
Val Val Asp Glu Ser Cys Trp Ser Asp Leu Glu Phe Cys Lys Ser Thr
```

```
                    145                 150                      155
AAG AAC TGG TAT TGC TAC GGC AAG GCA GTG GCG GAG AAG GCC GCT TGG       651
Lys Asn Trp Tyr Cys Tyr Gly Lys Ala Val Ala Glu Lys Ala Ala Trp
                160                 165                 170

CCA GAG GGC AAG GAG AGA GGG GTT GAC CTC GTG GTG ATT AAC CCT GTG       699
Pro Glu Gly Lys Glu Arg Gly Val Asp Leu Val Val Ile Asn Pro Val
            175                 180                 185

CTC GTG CTT GGA CCG CTC CTT CAG TCG ACG ATC AAT GCG AGC ATC ATC       747
Leu Val Leu Gly Pro Leu Leu Gln Ser Thr Ile Asn Ala Ser Ile Ile
            190                 195                 200

CAC ATC CTC AAG TAC TTG ACT GGC TCA GCC AAG ACC TAC GCC AAC TCG       795
His Ile Leu Lys Tyr Leu Thr Gly Ser Ala Lys Thr Tyr Ala Asn Ser
205                 210                 215                 220

GTC CAG GCG TAC GTG CAC GTC AAG GAC GTC GCG CTT GCC CAC GTC CTT       843
Val Gln Ala Tyr Val His Val Lys Asp Val Ala Leu Ala His Val Leu
                225                 230                 235

GTC TTG GAG ACC CCA TCC GCC TCA GGC CGC TAT TTG TGC GCC GAG AGC       891
Val Leu Glu Thr Pro Ser Ala Ser Gly Arg Tyr Leu Cys Ala Glu Ser
                240                 245                 250

GTC CTC CAC CGT GGC GAT GTG GTG GAA ATC CTT GCC AAG TTC TTC CCT       939
Val Leu His Arg Gly Asp Val Val Glu Ile Leu Ala Lys Phe Phe Pro
            255                 260                 265

GAG TAT AAT GTA CCG ACC AAG TGC TCT GAT GAG GTG AAC CCA AGA GTA       987
Glu Tyr Asn Val Pro Thr Lys Cys Ser Asp Glu Val Asn Pro Arg Val
270                 275                 280

AAA CCA TAC AAG TTC TCC AAC CAG AAG CTG AGA GAC TTG GGG CTC GAG      1035
Lys Pro Tyr Lys Phe Ser Asn Gln Lys Leu Arg Asp Leu Gly Leu Glu
285                 290                 295                 300

TTC ACC CCG GTG AAG CAG TGC CTG TAC GAA ACT GTC AAG AGC TTG CAG      1083
Phe Thr Pro Val Lys Gln Cys Leu Tyr Glu Thr Val Lys Ser Leu Gln
                305                 310                 315

GAG AAA GGC CAC CTA CCA GTC CCC TCC CCG CCG GAA GAT TCG GTG CGT      1131
Glu Lys Gly His Leu Pro Val Pro Ser Pro Pro Glu Asp Ser Val Arg
                320                 325                 330

ATT CAG GGA TGATCTTAGA TCCATCACGG TGCGCATTTG AAATCCGGAG              1180
Ile Gln Gly
        335

AAATGAGAGA AACATGTGGG AATTTGTTTG TACTTTTCTA AGTCAAACCT GGAGATACCA    1240

ACCCTGAGTT CTGCATTGGA ATGGAAGTTG TCAATTGTTC CAAAAAAAAA AAAAAAA       1297

(2) INFORMATION FOR SEQ ID NO:2:

(i) SEQUENCE CHARACTERISTICS:
        (A) LENGTH: 335 amino acids
        (B) TYPE: amino acid
        (D) TOPOLOGY: linear (ii) MOLECULE TYPE: protein (xi) SEQUENCE DESCRIPTION: SEQ ID NO:2:

Met Pro Val Asp Ala Leu Pro Gly Ser Gly Gln Thr Val Cys Val Thr
 1               5                  10                  15

Gly Ala Gly Gly Phe Ile Ala Ser Trp Ile Val Lys Leu Leu Leu Glu
                20                  25                  30

Arg Gly Tyr Thr Val Arg Gly Thr Val Arg Asn Pro Asp Asp Pro Lys
            35                  40                  45

Asn Gly His Leu Arg Asp Leu Glu Gly Ala Ser Glu Arg Leu Thr Leu
        50                  55                  60

Tyr Lys Gly Asp Leu Met Asp Tyr Gly Ser Leu Glu Glu Ala Ile Lys
65                  70                  75                  80
```

-continued

```
Gly Cys Asp Gly Val Val His Thr Ala Ser Pro Val Thr Asp Pro
                85                  90                  95

Glu Gln Met Val Glu Pro Ala Val Ile Gly Thr Lys Asn Val Ile Val
            100                 105                 110

Ala Ala Ala Glu Ala Lys Val Arg Arg Val Val Phe Thr Ser Ser Ile
        115                 120                 125

Gly Ala Val Thr Met Asp Pro Asn Arg Ala Asp Val Val Asp Glu
130                 135                 140

Ser Cys Trp Ser Asp Leu Glu Phe Cys Lys Ser Thr Lys Asn Trp Tyr
145                 150                 155                 160

Cys Tyr Gly Lys Ala Val Ala Glu Lys Ala Ala Trp Pro Glu Gly Lys
                165                 170                 175

Glu Arg Gly Val Asp Leu Val Val Ile Asn Pro Val Leu Val Leu Gly
            180                 185                 190

Pro Leu Leu Gln Ser Thr Ile Asn Ala Ser Ile Ile His Ile Leu Lys
        195                 200                 205

Tyr Leu Thr Gly Ser Ala Lys Thr Tyr Ala Asn Ser Val Gln Ala Tyr
    210                 215                 220

Val His Val Lys Asp Val Ala Leu Ala His Val Leu Val Leu Glu Thr
225                 230                 235                 240

Pro Ser Ala Ser Gly Arg Tyr Leu Cys Ala Glu Ser Val Leu His Arg
                245                 250                 255

Gly Asp Val Val Glu Ile Leu Ala Lys Phe Phe Pro Glu Tyr Asn Val
            260                 265                 270

Pro Thr Lys Cys Ser Asp Glu Val Asn Pro Arg Val Lys Pro Tyr Lys
        275                 280                 285

Phe Ser Asn Gln Lys Leu Arg Asp Leu Gly Leu Glu Phe Thr Pro Val
    290                 295                 300

Lys Gln Cys Leu Tyr Glu Thr Val Lys Ser Leu Gln Glu Lys Gly His
305                 310                 315                 320

Leu Pro Val Pro Ser Pro Pro Glu Asp Ser Val Arg Ile Gln Gly
                325                 330                 335
```

(2) INFORMATION FOR SEQ ID NO:3:

(i) SEQUENCE CHARACTERISTICS:
        (A) LENGTH: 1376 base pairs
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (ix) FEATURE:
        (A) NAME/KEY: CDS
        (B) LOCATION: 99..1112

(xi) SEQUENCE DESCRIPTION: SEQ ID NO:3:

```
GAAAACACAC CTCCTCTCTT CTTTGTCTCT GTCTGTTCTC CACTTTCCCA GTCACCAAAC      60

TCGTATGCAT ATAATTACAT TTATCTAAAT ATAACAAC ATG CCT GTT GAT GCT         113
                                          Met Pro Val Asp Ala
                                            1               5

TCA TCA CTT TCA GGC CAA GGC CAA ACT ATC TGT GTC ACC GGG GGT GGT       161
Ser Ser Leu Ser Gly Gln Gly Gln Thr Ile Cys Val Thr Gly Gly Gly
         10                  15                  20
```

```
GGT TTC ATT GCT TCT TGG ATG GTT AAA CTT CTT TTA GAT AAA GGT TAC         209
Gly Phe Ile Ala Ser Trp Met Val Lys Leu Leu Leu Asp Lys Gly Tyr
                25                  30                  35

ACT GTT AGA GGA ACT GCG AGG AAC CCA GCT GAT CCC AAG AAT TCT CAT         257
Thr Val Arg Gly Thr Ala Arg Asn Pro Ala Asp Pro Lys Asn Ser His
        40                  45                  50

TTG AGG GAG CTT GAA GGA GCT GAA GAA AGA TTA ACT TTA TGC AAA GCT         305
Leu Arg Glu Leu Glu Gly Ala Glu Glu Arg Leu Thr Leu Cys Lys Ala
    55                  60                  65

GAT CTT CTT GAT TAT GAG TCT CTT AAA GAG GGT ATT CAA GGG TGT GAT         353
Asp Leu Leu Asp Tyr Glu Ser Leu Lys Glu Gly Ile Gln Gly Cys Asp
70                  75                  80                  85

GGT GTT TTC CAC ACT GCT TCT CCT GTC ACA GAT GAT CCG GAA GAA ATG         401
Gly Val Phe His Thr Ala Ser Pro Val Thr Asp Asp Pro Glu Glu Met
            90                  95                 100

GTG GAG CCA GCA GTG AAC GGG ACC AAA AAT GTG ATA ATT GCG GCG GCT         449
Val Glu Pro Ala Val Asn Gly Thr Lys Asn Val Ile Ile Ala Ala Ala
               105                 110                 115

GAG GCC AAA GTC CGA CGA GTG GTG TTC ACG TCA TCA ATT GGC GCT GTG         497
Glu Ala Lys Val Arg Arg Val Val Phe Thr Ser Ser Ile Gly Ala Val
       120                 125                 130

TAC ATG GAT CCC AAT AAG GGC CCA GAT GTT GTC ATT GAT GAG TCT TGC         545
Tyr Met Asp Pro Asn Lys Gly Pro Asp Val Val Ile Asp Glu Ser Cys
   135                 140                 145

TGG AGT GAT CTT GAA TTC TGC AAG AAC ACC AAG AAT TGG TAT TGC TAT         593
Trp Ser Asp Leu Glu Phe Cys Lys Asn Thr Lys Asn Trp Tyr Cys Tyr
150                 155                 160                 165

GGA AAG GCT GTG GCA GAA CAA GCT GCA TGG GAT ATG GCT AAG GAG AAA         641
Gly Lys Ala Val Ala Glu Gln Ala Ala Trp Asp Met Ala Lys Glu Lys
               170                 175                 180

GGG GTG GAC CTA GTG GTG GTT AAC CCA GTG CTG GTG CTT GGA CCA TTG         689
Gly Val Asp Leu Val Val Val Asn Pro Val Leu Val Leu Gly Pro Leu
       185                 190                 195

TTG CAG CCC ACT GTC AAT GCT AGC ATC ACT CAC ATC CTC AAG TAC CTC         737
Leu Gln Pro Thr Val Asn Ala Ser Ile Thr His Ile Leu Lys Tyr Leu
   200                 205                 210

ACC GGC TCA GCC AAG ACA TAT GCT AAC TCT GTT CAA GCT TAT GTG CAT         785
Thr Gly Ser Ala Lys Thr Tyr Ala Asn Ser Val Gln Ala Tyr Val His
215                 220                 225

GTT AGG GAT GTG GCA CTA GCC CAC ATT TTA GTC TTT GAG ACG CCT TCC         833
Val Arg Asp Val Ala Leu Ala His Ile Leu Val Phe Glu Thr Pro Ser
230                 235                 240                 245

GCC TCC GGC CGT TAC CTT TGC TCT GAG AGC GTT CTC CAC CGT GGA GAG         881
Ala Ser Gly Arg Tyr Leu Cys Ser Glu Ser Val Leu His Arg Gly Glu
               250                 255                 260

GTG GTG GAA ATC CTT GCA AAG TTC TTC CCT GAG TAC CCC ATC CCT ACC         929
Val Val Glu Ile Leu Ala Lys Phe Phe Pro Glu Tyr Pro Ile Pro Thr
       265                 270                 275

AAG TGC TCA GAT GAG AAG AAC CCA AGA AAA CAA CCT TAC AAG TTC TCA         977
Lys Cys Ser Asp Glu Lys Asn Pro Arg Lys Gln Pro Tyr Lys Phe Ser
   280                 285                 290

AAC CAG AAG CTA AGG GAT CTG GGT TTC GAA TTC ACC CCA GTA AAG CAG        1025
Asn Gln Lys Leu Arg Asp Leu Gly Phe Glu Phe Thr Pro Val Lys Gln
295                 300                 305

TGT CTG TAT GAA ACT GTT AAG AGT TTG CAG GAA AAG GGT CAC CTT CCA        1073
Cys Leu Tyr Glu Thr Val Lys Ser Leu Gln Glu Lys Gly His Leu Pro
310                 315                 320                 325

ATC CCA AAA CAA GCT GCA GAA GAG TCT TTG AAA ATT CAA TAAGGCCTCT        1122
Ile Pro Lys Gln Ala Ala Glu Glu Ser Leu Lys Ile Gln
               330                 335
```

-continued

```
TGGAACTATT TATTAGGATT GTTCCATACC CCAAGTTTGG ATCGCAAATG CTAGGGAAAG    1182

GAGCATATTA AAGAATGCCA ATGTGCAGGT GTTTTAGTAT TTTACATGAA GAACTCTGAT    1242

TATCCTTGTG CTTATAATAA TTTTTTTCAA GTGAGTGTCT TCAAATGTTC AACTTGTATT    1302

TGTGGTTGTC TAACTTTATC CAGTTTCAAT ATAAAAGAGG AACGATTCTA TGTCTTAAAA    1362

AAAAAAAAAA AAAA                                                       1376
```

(2) INFORMATION FOR SEQ ID NO:4:

(i) SEQUENCE CHARACTERISTICS:
        (A) LENGTH: 338 amino acids
        (B) TYPE: amino acid
        (D) TOPOLOGY: linear (ii) MOLECULE TYPE: protein (xi) SEQUENCE DESCRIPTION: SEQ ID NO:4:

```
Met Pro Val Asp Ala Ser Ser Leu Ser Gly Gln Gly Gln Thr Ile Cys
 1               5                  10                  15

Val Thr Gly Gly Gly Gly Phe Ile Ala Ser Trp Met Val Lys Leu Leu
            20                  25                  30

Leu Asp Lys Gly Tyr Thr Val Arg Gly Thr Ala Arg Asn Pro Ala Asp
        35                  40                  45

Pro Lys Asn Ser His Leu Arg Glu Leu Glu Gly Ala Glu Glu Arg Leu
    50                  55                  60

Thr Leu Cys Lys Ala Asp Leu Leu Asp Tyr Glu Ser Leu Lys Glu Gly
65                  70                  75                  80

Ile Gln Gly Cys Asp Gly Val Phe His Thr Ala Ser Pro Val Thr Asp
                85                  90                  95

Asp Pro Glu Glu Met Val Glu Pro Ala Val Asn Gly Thr Lys Asn Val
            100                 105                 110

Ile Ile Ala Ala Ala Glu Ala Lys Val Arg Arg Val Val Phe Thr Ser
        115                 120                 125

Ser Ile Gly Ala Val Tyr Met Asp Pro Asn Lys Gly Pro Asp Val Val
    130                 135                 140

Ile Asp Glu Ser Cys Trp Ser Asp Leu Glu Phe Cys Lys Asn Thr Lys
145                 150                 155                 160

Asn Trp Tyr Cys Tyr Gly Lys Ala Val Ala Glu Gln Ala Ala Trp Asp
                165                 170                 175

Met Ala Lys Glu Lys Gly Val Asp Leu Val Val Val Asn Pro Val Leu
            180                 185                 190

Val Leu Gly Pro Leu Leu Gln Pro Thr Val Asn Ala Ser Ile Thr His
        195                 200                 205

Ile Leu Lys Tyr Leu Thr Gly Ser Ala Lys Thr Tyr Ala Asn Ser Val
    210                 215                 220

Gln Ala Tyr Val His Val Arg Asp Val Ala Leu Ala His Ile Leu Val
225                 230                 235                 240

Phe Glu Thr Pro Ser Ala Ser Gly Arg Tyr Leu Cys Ser Glu Ser Val
                245                 250                 255

Leu His Arg Gly Glu Val Val Glu Ile Leu Ala Lys Phe Phe Pro Glu
            260                 265                 270

Tyr Pro Ile Pro Thr Lys Cys Ser Asp Glu Lys Asn Pro Arg Lys Gln
        275                 280                 285

Pro Tyr Lys Phe Ser Asn Gln Lys Leu Arg Asp Leu Gly Phe Glu Phe
    290                 295                 300

Thr Pro Val Lys Gln Cys Leu Tyr Glu Thr Val Lys Ser Leu Gln Glu
```

```
                305                 310                 315                 320
Lys Gly His Leu Pro Ile Pro Lys Gln Ala Ala Glu Ser Leu Lys
                        325                 330                 335

Ile Gln (2) INFORMATION FOR SEQ ID NO:5:

(i) SEQUENCE CHARACTERISTICS:
        (A) LENGTH: 1273 base pairs
        (B) TYPE: nucleic acid
        (C) STRANDEDNESS: single
        (D) TOPOLOGY: linear (ii) MOLECULE TYPE: cDNA to mRNA (iii) HYPOTHETICAL: NO (iv) ANTI-SENSE: NO (ix) FEATURE:
        (A) NAME/KEY: CDS
        (B) LOCATION: 66..1091

(xi) SEQUENCE DESCRIPTION: SEQ ID NO:5:

TCGTAGCTCT TCCCTTTCAC CAACAAGCTA GTTTAGACAA GTACAGTGGT ACTGTAAGAG      60

CAACA ATG ACC GTT GTC GAC GCC GCC GCG CCG CAG CTG CCT GGC CAT         107
      Met Thr Val Val Asp Ala Ala Ala Pro Gln Leu Pro Gly His
      1               5                   10

GGG CAG ACC GTG TGC GTC ACC GGC GCC GCG GGG TAC ATC GCG TCG GGG       155
Gly Gln Thr Val Cys Val Thr Gly Ala Ala Gly Tyr Ile Ala Ser Gly
15                  20                  25                  30

CTC GTC AAG CTG CTC CTG GAG AGA GGC TAC ACC GTG AAG GGC ACA GTG       203
Leu Val Lys Leu Leu Leu Glu Arg Gly Tyr Thr Val Lys Gly Thr Val
                35                  40                  45

AGG AAC CCA GAT GAT CCC AAG AAC GCC CAC CTG AAG GCG CTG GAC GGC       251
Arg Asn Pro Asp Asp Pro Lys Asn Ala His Leu Lys Ala Leu Asp Gly
            50                  55                  60

GCC ACC AAG AGG CTG ATC CTC TGC AAA GCC GAC CTC CTC GAC TAC GAC       299
Ala Thr Lys Arg Leu Ile Leu Cys Lys Ala Asp Leu Leu Asp Tyr Asp
        65                  70                  75

GCC ATA TGC GCC GCC GTC GAG GGC TGC CAC GGC GTG TTC CAC ACC GCC       347
Ala Ile Cys Ala Ala Val Glu Gly Cys His Gly Val Phe His Thr Ala
    80                  85                  90

TCT CCA GTC ACC GAT GAT CCT GAG CAG ATG GTG GAG CCG GCG GTG CGG       395
Ser Pro Val Thr Asp Asp Pro Glu Gln Met Val Glu Pro Ala Val Arg
95                  100                 105                 110

GGC ACG GAG TAC GTG ATC AAC GCG GCA GCG GAT GCG GGA ACG GTG CGC       443
Gly Thr Glu Tyr Val Ile Asn Ala Ala Ala Asp Ala Gly Thr Val Arg
                115                 120                 125

CGG GTG GTG TTC ACG TCG TCA ATC GGT GCC ATC ACC ATG GAC CCC AAC       491
Arg Val Val Phe Thr Ser Ser Ile Gly Ala Ile Thr Met Asp Pro Asn
            130                 135                 140

CGC GGT CCT GAC GTA GTC GTC AAT GAG TCC TGC TGG AGC GAC CTC GAA       539
Arg Gly Pro Asp Val Val Val Asn Glu Ser Cys Trp Ser Asp Leu Glu
        145                 150                 155

TTC TGC AAG AAA ACC AAG AAC TGG TAC TGC TAC GGC AAG GCC GTG GCG       587
Phe Cys Lys Lys Thr Lys Asn Trp Tyr Cys Tyr Gly Lys Ala Val Ala
    160                 165                 170

GAG CAG GCT GCG TGG GAG GCG GCC AGG AAG CGC GGC ATC GAC CTC GTC       635
Glu Gln Ala Ala Trp Glu Ala Ala Arg Lys Arg Gly Ile Asp Leu Val
175                 180                 185                 190

GTC GTG AAC CCT GTG CTC GTG GTA GGG CCG CTG CTG CAA CCA ACG GTG       683
Val Val Asn Pro Val Leu Val Val Gly Pro Leu Leu Gln Pro Thr Val
```

-continued

```
                195                 200                     205
AAC GCT AGC GCC GCA CAC ATC CTC AAG TAC CTC GAC GGC TCG GCC AAG        731
Asn Ala Ser Ala Ala His Ile Leu Lys Tyr Leu Asp Gly Ser Ala Lys
            210                 215                 220

AAG TAC GCC AAC GCT GTG CAG TCA TAC GTA GAC GTG CGT GAC GTA GCC        779
Lys Tyr Ala Asn Ala Val Gln Ser Tyr Val Asp Val Arg Asp Val Ala
            225                 230                 235

GGC GCG CAC ATC CGG GTG TTC GAG GCG CCT GAG GCG TCG GGC CGG TAC        827
Gly Ala His Ile Arg Val Phe Glu Ala Pro Glu Ala Ser Gly Arg Tyr
            240                 245                 250

CTC TGC GCC GAG CGC GTG CTG CAC CGT GGG GAC GTT GTC CAA ATC CTC        875
Leu Cys Ala Glu Arg Val Leu His Arg Gly Asp Val Val Gln Ile Leu
255                 260                 265                 270

AGC AAA CTC TTG CCT GAG TAC CCT GTG CCA ACA AGG TGC TCT GAT GAA        923
Ser Lys Leu Leu Pro Glu Tyr Pro Val Pro Thr Arg Cys Ser Asp Glu
                275                 280                 285

GTG AAC CCA CGG AAG CAG CCT TAT AAG ATG TCC AAC CAG AAG CTG CAG        971
Val Asn Pro Arg Lys Gln Pro Tyr Lys Met Ser Asn Gln Lys Leu Gln
            290                 295                 300

GAT CTT GGC CTC CAG TTC ACT CCT GTG AAC GAC TCT CTG TAT GAG ACC       1019
Asp Leu Gly Leu Gln Phe Thr Pro Val Asn Asp Ser Leu Tyr Glu Thr
            305                 310                 315

GTG AAG AGC CTC CAG GAG AAG GGA CAT CTC CTA GTA CCA AGC AAA CCC       1067
Val Lys Ser Leu Gln Glu Lys Gly His Leu Leu Val Pro Ser Lys Pro
320                 325                 330

GAG GGA TTA AAC GGT GTA ACG GCA TGATACTGCT AAAGAAGCAG CAGAGTTCAC      1121
Glu Gly Leu Asn Gly Val Thr Ala
335                 340

GTGCTCCTGT AACATGGTCA AACATGAGTT GTTTTTCTGT ATAAATTCTA TCCAGTATCG      1181

TGTTATTTAA GTGAACTAAG AGAACAGAAT ATTGTATCAT CTTCGATGTC CAATACCTGG      1241

AAGTGATTTG TTTTGCCACC TAAAAAAAAA AA                                    1273
```

(2) INFORMATION FOR SEQ ID NO:6:

(i) SEQUENCE CHARACTERISTICS:
        (A) LENGTH: 342 amino acids
        (B) TYPE: amino acid
        (D) TOPOLOGY: linear (ii) MOLECULE TYPE: protein (xi) SEQUENCE DESCRIPTION: SEQ ID NO:6:

```
Met Thr Val Val Asp Ala Ala Pro Gln Leu Pro Gly His Gly Gln
 1               5                  10                  15

Thr Val Cys Val Thr Gly Ala Ala Gly Tyr Ile Ala Ser Gly Leu Val
                20                  25                  30

Lys Leu Leu Leu Glu Arg Gly Tyr Thr Val Lys Gly Thr Val Arg Asn
            35                  40                  45

Pro Asp Asp Pro Lys Asn Ala His Leu Lys Ala Leu Asp Gly Ala Thr
        50                  55                  60

Lys Arg Leu Ile Leu Cys Lys Ala Asp Leu Leu Asp Tyr Asp Ala Ile
65                  70                  75                  80

Cys Ala Ala Val Glu Gly Cys His Gly Val Phe His Thr Ala Ser Pro
                85                  90                  95

Val Thr Asp Asp Pro Glu Gln Met Val Glu Pro Ala Val Arg Gly Thr
            100                 105                 110

Glu Tyr Val Ile Asn Ala Ala Asp Ala Gly Thr Val Arg Arg Val
            115                 120                 125
```

```
Val Phe Thr Ser Ser Ile Gly Ala Ile Thr Met Asp Pro Asn Arg Gly
    130                 135                 140

Pro Asp Val Val Val Asn Glu Ser Cys Trp Ser Asp Leu Glu Phe Cys
145                 150                 155                 160

Lys Lys Thr Lys Asn Trp Tyr Cys Tyr Gly Lys Ala Val Ala Glu Gln
                165                 170                 175

Ala Ala Trp Glu Ala Ala Arg Lys Arg Gly Ile Asp Leu Val Val Val
            180                 185                 190

Asn Pro Val Leu Val Val Gly Pro Leu Leu Gln Pro Thr Val Asn Ala
        195                 200                 205

Ser Ala Ala His Ile Leu Lys Tyr Leu Asp Gly Ser Ala Lys Lys Tyr
    210                 215                 220

Ala Asn Ala Val Gln Ser Tyr Val Asp Val Arg Asp Val Ala Gly Ala
225                 230                 235                 240

His Ile Arg Val Phe Glu Ala Pro Glu Ala Ser Gly Arg Tyr Leu Cys
                245                 250                 255

Ala Glu Arg Val Leu His Arg Gly Asp Val Val Gln Ile Leu Ser Lys
            260                 265                 270

Leu Leu Pro Glu Tyr Pro Val Pro Thr Arg Cys Ser Asp Glu Val Asn
        275                 280                 285

Pro Arg Lys Gln Pro Tyr Lys Met Ser Asn Gln Lys Leu Gln Asp Leu
    290                 295                 300

Gly Leu Gln Phe Thr Pro Val Asn Asp Ser Leu Tyr Glu Thr Val Lys
305                 310                 315                 320

Ser Leu Gln Glu Lys Gly His Leu Leu Val Pro Ser Lys Pro Glu Gly
                325                 330                 335

Leu Asn Gly Val Thr Ala
            340

(2) INFORMATION FOR SEQ ID NO:7:

(i) SEQUENCE CHARACTERISTICS:
        (A) LENGTH: 1293 base pairs
        (B) TYPE: nucleic acid
        (C) STRANDEDNESS: single
        (D) TOPOLOGY: linear (ii) MOLECULE TYPE: cDNA to mRNA (iii) HYPOTHETICAL: NO (iv) ANTI-SENSE: NO (ix) FEATURE:
        (A) NAME/KEY: CDS
        (B) LOCATION: 95..1108

(xi) SEQUENCE DESCRIPTION: SEQ ID NO:7:

CCGAGCCTAT TCTTCCCTA TATCCACTCA TCCTTGTCTT ATATCATCAT CATCATCATC       60

TACCTAAACC TGAGCTCAAC AGAAAAGTAA TACC ATG CCG TCA GTT TCC GGC         112
                                     Met Pro Ser Val Ser Gly
                                       1               5

CAA ATC GTT TGT GTT ACT GGC GCC GGA GGT TTC ATC GCC TCT TGG CTC       160
Gln Ile Val Cys Val Thr Gly Ala Gly Gly Phe Ile Ala Ser Trp Leu
        10                  15                  20

GTT AAA ATT CTT CTG GAA AAA GGC TAC ACT GTT AGA GGA ACA GTA CGA       208
Val Lys Ile Leu Leu Glu Lys Gly Tyr Thr Val Arg Gly Thr Val Arg
    25                  30                  35

AAT CCA GAT GAT CGA AAA AAT AGT CAT TTG AGG GAG CTT GAA CGA GCA       256
Asn Pro Asp Asp Arg Lys Asn Ser His Leu Arg Glu Leu Glu Arg Ala
40                  45                  50
```

```
AAA GAG ACA TTG ACT CTG TGC AGA GCT GAT CTT CTT GAT TTT CAG AGT          304
Lys Glu Thr Leu Thr Leu Cys Arg Ala Asp Leu Leu Asp Phe Gln Ser
 55                  60                  65                  70

TTG CGA GAA GCA ATC AGC GGC TGT GAC GGA GTT TTC CAC ACA CGT TCT          352
Leu Arg Glu Ala Ile Ser Gly Cys Asp Gly Val Phe His Thr Arg Ser
                     75                  80                  85

CCT GTC ACT GAT GAT CCA GAA CAA ATG GTG GAG CCA GCA GTT ATT GGT          400
Pro Val Thr Asp Asp Pro Glu Gln Met Val Glu Pro Ala Val Ile Gly
                 90                  95                 100

ACA AAG AAT GTG ATA ACG GCA GCA GAG GCC AAG GTG CGA CGT GTG              448
Thr Lys Asn Val Ile Thr Ala Ala Glu Ala Lys Val Arg Arg Val
            105                 110                 115

GTG TTC ACT TCG TCA ATT GGT GCT GTG TAT ATG GAC CCA AAC AGG GAC          496
Val Phe Thr Ser Ser Ile Gly Ala Val Tyr Met Asp Pro Asn Arg Asp
    120                 125                 130

CCT GAT AAG GTT GTC GAC GAG ACT TGT TGG AGT GAT CCT GAC TTC TGC          544
Pro Asp Lys Val Val Asp Glu Thr Cys Trp Ser Asp Pro Asp Phe Cys
135                 140                 145                 150

AAA AAC ACC AAG AAT TGG TAT TGT TAT GGG AAG ATG GTG GCA GAA CAA          592
Lys Asn Thr Lys Asn Trp Tyr Cys Tyr Gly Lys Met Val Ala Glu Gln
                155                 160                 165

GCA GCA TGG GAC GAA GCA AGG GAG AAA GGA GTC GAT TTG GTG GCA ATC          640
Ala Ala Trp Asp Glu Ala Arg Glu Lys Gly Val Asp Leu Val Ala Ile
            170                 175                 180

AAC CCA GTG TTG GTG CTT GGA CCA CTG CTC CAA CAG AAT GTG AAT GCC          688
Asn Pro Val Leu Val Leu Gly Pro Leu Leu Gln Gln Asn Val Asn Ala
        185                 190                 195

AGT GTT CTT CAC ATC CAC AAG TAC CTA ACT GGC TCT GCT AAA ACA TAT          736
Ser Val Leu His Ile His Lys Tyr Leu Thr Gly Ser Ala Lys Thr Tyr
    200                 205                 210

ACG TCC AAT TCA CTT CAG GCA TAT GTT CAT GTT AGG GAT GTG GCT TTA          784
Thr Ser Asn Ser Leu Gln Ala Tyr Val His Val Arg Asp Val Ala Leu
215                 220                 225                 230

CGT CAC ATA CTT GTG TAC GAG ACA CCT TCT GCA TCT GGC CGT TAT CTC          832
Arg His Ile Leu Val Tyr Glu Thr Pro Ser Ala Ser Gly Arg Tyr Leu
                235                 240                 245

TGT GCC GAG AGT GTG CTG CAT CGC TGC GAT GTG GTT GAA ATT CTC GCC          880
Cys Ala Glu Ser Val Leu His Arg Cys Asp Val Val Glu Ile Leu Ala
            250                 255                 260

AAA TTC TTC CCG GAG TAT CCT ATC CCC ACC AAG TGT TCA GAT GTG ACG          928
Lys Phe Phe Pro Glu Tyr Pro Ile Pro Thr Lys Cys Ser Asp Val Thr
        265                 270                 275

AAG CCA AGG GTA AAA CCG TAC AAA TTC TCA AAC CAA AAG CTA AAG GAT          976
Lys Pro Arg Val Lys Pro Tyr Lys Phe Ser Asn Gln Lys Leu Lys Asp
    280                 285                 290

TTG GGT CTG GAG TTT ACA CCA GTA CAA TGC TTA TAT GAA ACG GTG AAG         1024
Leu Gly Leu Glu Phe Thr Pro Val Gln Cys Leu Tyr Glu Thr Val Lys
295                 300                 305                 310

AGT CTA CAA GAG AAA GGT CAC CTT CCA ATT CCT ACT CAA AAG GAT GAG         1072
Ser Leu Gln Glu Lys Gly His Leu Pro Ile Pro Thr Gln Lys Asp Glu
                315                 320                 325

ATT ATT CGA ATT CAG TCT GAG AAA TTC AGA AGC TCT TAGCATGTAT             1118
Ile Ile Arg Ile Gln Ser Glu Lys Phe Arg Ser Ser
            330                 335

TGAGGAAAAG GGATCAATGG TTAAAGTTGA CCATGGCGTT GTCCCTTTAT GTACCAAGAC       1178

CAAATGCACC TAGAAATTTA CTTGTCTACT CTGTTGTACT TTTACTTGTC ATGGAAATGT       1238

TTTTAGTGTT TTCATTGTTA TGAGATATAT TTTGGTGTAA AAAAAAAAAA AAAAA           1293
```

(2) INFORMATION FOR SEQ ID NO:8:

(i) SEQUENCE CHARACTERISTICS:
        (A) LENGTH: 338 amino acids
        (B) TYPE: amino acid
        (D) TOPOLOGY: linear (ii) MOLECULE TYPE: protein (xi) SEQUENCE DESCRIPTION: SEQ ID NO:8:

```
Met Pro Ser Val Ser Gly Gln Ile Val Cys Val Thr Gly Ala Gly Gly
 1               5                  10                  15

Phe Ile Ala Ser Trp Leu Val Lys Ile Leu Leu Glu Lys Gly Tyr Thr
            20                  25                  30

Val Arg Gly Thr Val Arg Asn Pro Asp Asp Arg Lys Asn Ser His Leu
        35                  40                  45

Arg Glu Leu Glu Arg Ala Lys Glu Thr Leu Thr Leu Cys Arg Ala Asp
    50                  55                  60

Leu Leu Asp Phe Gln Ser Leu Arg Glu Ala Ile Ser Gly Cys Asp Gly
65                  70                  75                  80

Val Phe His Thr Arg Ser Pro Val Thr Asp Asp Pro Glu Gln Met Val
                85                  90                  95

Glu Pro Ala Val Ile Gly Thr Lys Asn Val Ile Thr Ala Ala Ala Glu
            100                 105                 110

Ala Lys Val Arg Arg Val Val Phe Thr Ser Ser Ile Gly Ala Val Tyr
        115                 120                 125

Met Asp Pro Asn Arg Asp Pro Asp Lys Val Val Asp Glu Thr Cys Trp
    130                 135                 140

Ser Asp Pro Asp Phe Cys Lys Asn Thr Lys Asn Trp Tyr Cys Tyr Gly
145                 150                 155                 160

Lys Met Val Ala Glu Gln Ala Ala Trp Asp Glu Ala Arg Glu Lys Gly
                165                 170                 175

Val Asp Leu Val Ala Ile Asn Pro Val Leu Val Leu Gly Pro Leu Leu
            180                 185                 190

Gln Gln Asn Val Asn Ala Ser Val Leu His Ile His Lys Tyr Leu Thr
        195                 200                 205

Gly Ser Ala Lys Thr Tyr Thr Ser Asn Ser Leu Gln Ala Tyr Val His
    210                 215                 220

Val Arg Asp Val Ala Leu Arg His Ile Leu Val Tyr Glu Thr Pro Ser
225                 230                 235                 240

Ala Ser Gly Arg Tyr Leu Cys Ala Glu Ser Val Leu His Arg Cys Asp
                245                 250                 255

Val Val Glu Ile Leu Ala Lys Phe Phe Pro Glu Tyr Pro Ile Pro Thr
            260                 265                 270

Lys Cys Ser Asp Val Thr Lys Pro Arg Val Lys Pro Tyr Lys Phe Ser
        275                 280                 285

Asn Gln Lys Leu Lys Asp Leu Gly Leu Glu Phe Thr Pro Val Gln Cys
    290                 295                 300

Leu Tyr Glu Thr Val Lys Ser Leu Gln Gly Lys Gly His Leu Pro Ile
305                 310                 315                 320

Pro Thr Gln Lys Asp Glu Ile Ile Arg Ile Gln Ser Glu Lys Phe Arg
                325                 330                 335

Ser Ser
```

(2) INFORMATION FOR SEQ ID NO:9:

(i) SEQUENCE CHARACTERISTICS:

(A) LENGTH: 1297 base pairs
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (ix) FEATURE:
        (A) NAME/KEY: CDS
        (B) LOCATION: 136..1140

(xi) SEQUENCE DESCRIPTION: SEQ ID NO:9:

```
CGGCCGGGAC GACCCGTTCC TCTTCTTCCG GGTCACCGTC ACCATGTTAC ACAACATCTC         60

CGGCTAAAAA AAAAAGGAAA AAAAGCGCAA CCTCCACCTC CTGAACCCCT CTCCCCCCTC        120

GCCGGCAATC CCACC ATG CCC GTC GAC GCC CTC CCC GGT TCC GGC CAG ACC        171
                Met Pro Val Asp Ala Leu Pro Gly Ser Gly Gln Thr
                 1               5                  10

GTC TGC GTC ACC GGC GCC GGC GGG TTC ATC GCC TCC TGG ATT GTC AAG        219
Val Cys Val Thr Gly Ala Gly Gly Phe Ile Ala Ser Trp Ile Val Lys
         15                  20                  25

CTT CTC CTC GAG CGA GGC TAC ACC GTG CGA GGA ACC GTC AGG AAC CCA        267
Leu Leu Leu Glu Arg Gly Tyr Thr Val Arg Gly Thr Val Arg Asn Pro
     30                  35                  40

GAC GAC CCG AAG AAT GGT CAT CTG AGA GAT CTG GAA GGA GCC AGC GAG        315
Asp Asp Pro Lys Asn Gly His Leu Arg Asp Leu Glu Gly Ala Ser Glu
 45                  50                  55                  60

AGG CTG ACG CTG TAC AAG GGT GAT CTG ATG GAC GAC GGG AGC TTG GAA        363
Arg Leu Thr Leu Tyr Lys Gly Asp Leu Met Asp Asp Gly Ser Leu Glu
                 65                  70                  75

GAA GCC ATC AAG GGG TGC GAC GGC GTC GTC CAC ACC GCC TCT CCG GTC        411
Glu Ala Ile Lys Gly Cys Asp Gly Val Val His Thr Ala Ser Pro Val
         80                  85                  90

ACC GAC GAT CCT GAG CAA ATG GTG GAG CCA GCG GTG ATC GGG ACG AAA        459
Thr Asp Asp Pro Glu Gln Met Val Glu Pro Ala Val Ile Gly Thr Lys
             95                 100                 105

AAT GTG ATC GTC GCA GCG GCG GAG GCC AAG GTC CGG CGG GTT GTG TTC        507
Asn Val Ile Val Ala Ala Ala Glu Ala Lys Val Arg Arg Val Val Phe
 110                 115                 120

ACC TCC TCC ATC GGT GCA GTC ACC ATG GAC CCC AAC CGG GCA GAC GTT        555
Thr Ser Ser Ile Gly Ala Val Thr Met Asp Pro Asn Arg Ala Asp Val
125                 130                 135                 140

GTG GTG GAC GAG TCT TGT TGG AGC GAC CTC GAA TTT TGC AAG AGC ACT        603
Val Val Asp Glu Ser Cys Trp Ser Asp Leu Glu Phe Cys Lys Ser Thr
                145                 150                 155

AAG AAC TGG TAT TGC TAC GGC AAG GCA GTG GCG GAG AAG GCC GCT TGG        651
Lys Asn Trp Tyr Cys Tyr Gly Lys Ala Val Ala Glu Lys Ala Ala Trp
        160                 165                 170

CCA GAG GGC AAG GAG AGA GGG GTT GAC CTC GTG GTG ATT AAC CCT GTG        699
Pro Glu Gly Lys Glu Arg Gly Val Asp Leu Val Val Ile Asn Pro Val
    175                 180                 185

CTC GTG CTT GGA CCG CTC CTT CAG TCG ACG ATC AAT GCG AGC ATC ATC        747
Leu Val Leu Gly Pro Leu Leu Gln Ser Thr Ile Asn Ala Ser Ile Ile
190                 195                 200

CAC ATC CTC AAG TAC TTG ACT GGC TCA GCC AAG ACC TAC GCC AAC TCG        795
His Ile Leu Lys Tyr Leu Thr Gly Ser Ala Lys Thr Tyr Ala Asn Ser
205                 210                 215                 220

GTC CAG GCG TAC GTG CAC GTC AAG GAC GTC GCG CTT GCC CAC GTC CTT        843
Val Gln Ala Tyr Val His Val Lys Asp Val Ala Leu Ala His Val Leu
            225                 230                 235
```

```
GTC TTG GAG ACC CCA TCC GCC TCA GGC CGC TAT TTG TGC GCC GAG AGC        891
Val Leu Glu Thr Pro Ser Ala Ser Gly Arg Tyr Leu Cys Ala Glu Ser
            240                 245                 250

GTC CTC CAC CGT GGC GAT GTG GTG GAA ATC CTT GCC AAG TTC TTC CCT        939
Val Leu His Arg Gly Asp Val Val Glu Ile Leu Ala Lys Phe Phe Pro
            255                 260                 265

GAG TAT AAT GTA CCG ACC AAG TGC TCT GAT GAG GTG AAC CCA AGA GTA        987
Glu Tyr Asn Val Pro Thr Lys Cys Ser Asp Glu Val Asn Pro Arg Val
270                 275                 280

AAA CCA TAC AAG TTC TCC AAC CAG AAG CTG AGA GAC TTG GGG CTC GAG       1035
Lys Pro Tyr Lys Phe Ser Asn Gln Lys Leu Arg Asp Leu Gly Leu Glu
285                 290                 295                 300

TTC ACC CCG GTG AAG CAG TGC CTG TAC GAA ACT GTC AAG AGC TTG CAG       1083
Phe Thr Pro Val Lys Gln Cys Leu Tyr Glu Thr Val Lys Ser Leu Gln
            305                 310                 315

GAG AAA GGC CAC CTA CCA GTC CCC TCC CCG CCG GAA GAT TCG GTG CGT       1131
Glu Lys Gly His Leu Pro Val Pro Ser Pro Pro Glu Asp Ser Val Arg
            320                 325                 330

ATT CAG GGA TGATCTTAGA TCCATCACGG TGCGCATTTG TAATCCGGAG               1180
Ile Gln Gly
            335

AAATGAGAGA ACATGTGGG AATTTGTTTG TACTTTTCTA AGTCAAACCT GGAGATACCA      1240

ACCCTGAGTT CTGCATTGGA ATGGAAGTTG TCAATTGTTC CAAAAAAAAA AAAAAAA       1297

(2) INFORMATION FOR SEQ ID NO:10:

(i) SEQUENCE CHARACTERISTICS:
        (A) LENGTH: 335 amino acids
        (B) TYPE: amino acid
        (D) TOPOLOGY: linear (ii) MOLECULE TYPE: protein (xi) SEQUENCE DESCRIPTION: SEQ ID NO:10:

Met Pro Val Asp Ala Leu Pro Gly Ser Gly Gln Thr Val Cys Val Thr
1               5                   10                  15

Gly Ala Gly Gly Phe Ile Ala Ser Trp Ile Val Lys Leu Leu Leu Glu
            20                  25                  30

Arg Gly Tyr Thr Val Arg Gly Thr Val Arg Asn Pro Asp Asp Pro Lys
        35                  40                  45

Asn Gly His Leu Arg Asp Leu Glu Gly Ala Ser Glu Arg Leu Thr Leu
    50                  55                  60

Tyr Lys Gly Asp Leu Met Asp Asp Gly Ser Leu Glu Glu Ala Ile Lys
65                  70                  75                  80

Gly Cys Asp Gly Val Val His Thr Ala Ser Pro Val Thr Asp Asp Pro
                85                  90                  95

Glu Gln Met Val Glu Pro Ala Val Ile Gly Thr Lys Asn Val Ile Val
            100                 105                 110

Ala Ala Ala Glu Ala Lys Val Arg Arg Val Val Phe Thr Ser Ser Ile
        115                 120                 125

Gly Ala Val Thr Met Asp Pro Asn Arg Ala Asp Val Val Val Asp Glu
    130                 135                 140

Ser Cys Trp Ser Asp Leu Glu Phe Cys Lys Ser Thr Lys Asn Trp Tyr
145                 150                 155                 160

Cys Tyr Gly Lys Ala Val Ala Glu Lys Ala Ala Trp Pro Glu Gly Lys
                165                 170                 175

Glu Arg Gly Val Asp Leu Val Val Ile Asn Pro Val Leu Val Leu Gly
            180                 185                 190
```

```
Pro Leu Leu Gln Ser Thr Ile Asn Ala Ser Ile Ile His Ile Leu Lys
        195                 200                 205

Tyr Leu Thr Gly Ser Ala Lys Thr Tyr Ala Asn Ser Val Gln Ala Tyr
        210                 215                 220

Val His Val Lys Asp Val Ala Leu Ala His Val Leu Val Leu Glu Thr
225                 230                 235                 240

Pro Ser Ala Ser Gly Arg Tyr Leu Cys Ala Glu Ser Val Leu His Arg
                245                 250                 255

Gly Asp Val Val Glu Ile Leu Ala Lys Phe Phe Pro Glu Tyr Asn Val
                260                 265                 270

Pro Thr Lys Cys Ser Asp Glu Val Asn Pro Arg Val Lys Pro Tyr Lys
        275                 280                 285

Phe Ser Asn Gln Lys Leu Arg Asp Leu Gly Leu Glu Phe Thr Pro Val
        290                 295                 300

Lys Gln Cys Leu Tyr Glu Thr Val Lys Ser Leu Gln Glu Lys Gly His
305                 310                 315                 320

Leu Pro Val Pro Ser Pro Pro Glu Asp Ser Val Arg Ile Gln Gly
                325                 330                 335
```

DNA SEQUENCES CODING FOR A CINNAMOYL COA REDUCTASE AND THEIR USES IN THE FIELD OF REGULATING THE LIGNIN LEVELS OF PLANTS

FIELD OF THE INVENTION

A subject of the present invention is the use of DNA sequences coding for a cinnamoyl CoA reductase (CCR) in plants, or any fragment of these sequences, or also any sequence derived from the latter, or their complementary sequences, within the scope of the implementation of processes for the regulation of the lignin level in plants.

BACKGROUND OF THE INVENTION

Lignin is a complex heterogeneous aromatic polymer which waterproofs and reinforces the walls of certain plant cells.

Lignin is formed by the polymerization of free radicals derived from monolignols such as paracoumarylic, coniferylic and sinapylic alcohols (Higuchi, 1985, in Biosynthesis and degradation of wood components (T. Higuchi, ed), Academic Press, Orlando, Fla. pp. 141–160).

Lignins have a large variation in their relative monolignol levels, as a function of the species and the different tissues within the same plant.

This variation is probably due to and controlled by the different activities and specificities of substrates, of enzymes necessary for the biosynthesis of lignin monomers (Higuchi, 1985, mentioned above).

Beyond its role in the structure and development of plants, lignin represents a major component of the terrestrial biomass and assumes a great economic and ecological significance (Brown, 1985, J. Appl. Biochem. 7, 371–387; Whetten and Sederoff, 1991, Forest Ecology and Management, 43, 301–316).

With regard to the exploitation of the biomass, first and foremost it should be noted that lignin is a factor limiting the digestibility and nutritional yield of fodder crops. In fact, it is clearly demonstrated that the digestibility of fodder crops by ruminants, is inversely proportional to the lignin level of these plants, the nature of the lignins also being a determining factor in this phenomenon (Buxton and Roussel, 1988, Crop. Sci., 28, 553–558; Jung and Vogel, 1986, J. Anin. Sci., 62, 1703–1712).

Among the principle fodder crops in which it would be useful to reduce the level of lignins, there can be mentioned: alfalfa, fescue, maize, fodder used for silage . . . .

It should also be noted that high lignin levels are in part responsible for the limited quality of sunflower cakes intended for cattle food and the reduction in the viability of certain seeds in the horticultural domain.

It can also be emphasized that the intense lignification which occurs during the storage of plant organs after harvest, rapidly renders crops such as asparagus, yams, carrots, etc. unfit for consumption.

Moreover, it should also be noted that more than 50 million tons of lignins are extracted from ligneous material each year in the production of paper pulp in the paper industry. This extraction operation which is necessary to obtain cellulose is costly in terms of energy and secondarily polluting due to the chemical compounds employed in the extraction and which find their way into the environment (Dean & Eriksson, 1992, Holzforschung, 46, 135–147; Whetten and Sederoff, 1991, mentioned above).

To reduce the proportions of lignins (which depending on the species represent 20 to 30% of the dry material) to a few percent (2 to 5%) would represent an increase in yield, a substantial saving (chemical products) and would contribute to the improvement of the environment (reduction in pollution). Given the scale on which ligneous material is used, these effects would have extremely significant repercussions. In this case, the species concerned could be the poplar, the eucalyptus, *Acacia mangium*, the Casuarina genus and all the angiosperms and gymnosperms used in the production of paper pulp.

In the two fields considered, it is clear that the reduction of lignin levels must be moderate in order for the plant (or tree) to retain its characteristics of rigidity and its normal architecture, as the lignins which reinforce the cell walls play an important role in maintaining the upright habit of plants.

Natural variations in the levels of lignins observed in nature for the same species (difference which can range up to 6–8% of the dry mass between individuals) permit the reductions mentioned above.

The resistance to degradation of lignin, as well as the difficulties encountered in its extraction, are probably due to the complex structure of this polymer constituted by ether and carbon—carbon bonds between the monomers, as well as to the numerous chemical bonds existing between lignin and other components of the cell wall (Sarkanen and Ludwig, 1971, in Lignins: Occurrence, Formation, Structure and Reactions (K. V. Sarkanen and C. H. Ludwig eds) New York: Wiley—Interscience, pp. 1–18).

Starting from cinnamoyls-CoA, the biosynthesis of lignins in plants, is carried out in the following manner:

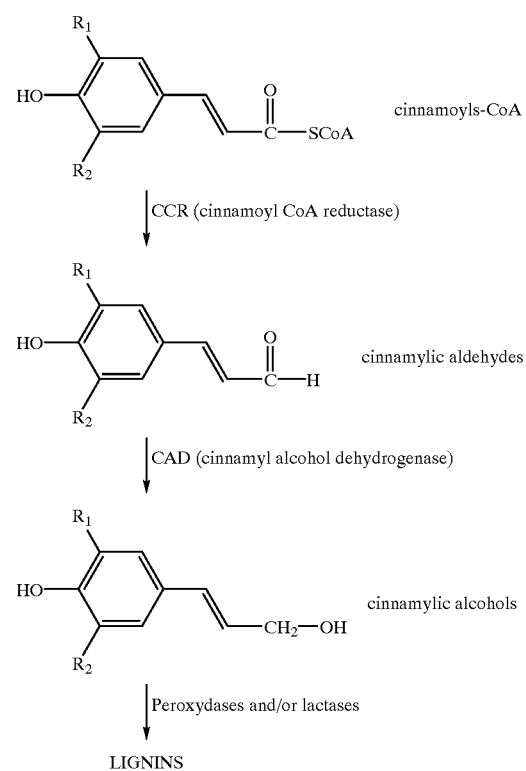

One approach, using the genetic engineering route, to try to reduce the level of lignins in plants, would consist of inhibiting the synthesis of one of the enzymes of the biosynthesis chain of these lignins indicated above.

A technique which is particularly appropriate within the scope of such an approach, is that of using anti sense mRNA capable of hybridizing with the mRNA coding for these enzymes, and as a consequence, of inhibiting, at least partially, the production of these enzymes from their corresponding mRNA.

Such an anti sense strategy, carried out using the gene coding for CAD in tobacco, was the subject of the European Patent Application No. 584 117, describing the use of anti sense mRNA capable of inhibiting the production of lignins in the plants by hybridizing with the mRNA coding for CAD in these plants.

The results at the level of the plants transformed in this way demonstrate a reduction in the activity of CAD, but paradoxically, the lignin levels show no change. Additional studies indicate that the lignins of the transformed plants are different from the control lignins, because the cinnamylic aldehydes are directly incorporated in the lignin polymer.

DESCRIPTION OF THE INVENTION

One of the aims of the present invention is precisely that of providing a process allowing the lignin levels in plants to be effectively regulated, either in the sense of an appreciable reduction in these levels relative to the normal levels in plants, or in the sense of an increase in these levels.

Another aim of the present invention is to provide the tools for the implementation of such a process, and more particularly usable constructions for the transformation of plants.

Another aim of the present invention is to provide genetically transformed plants, in particular fodder crops capable of being more digestible than untransformed plants, or also transformed plants or trees for the production of paper pulp, and from which the extraction of lignin would be easier and less polluting than in the case of untransformed trees.

Another aim of the present invention is that of providing transformed plants which are more resistant to attack from the environment, in particular parasitic attack, than untransformed plants are, or also transformed plants of a larger size, or of a smaller size (than that of untransformed plants).

A subject of the present invention is the use of recombinant nucleotide sequences containing one (or more) coding region(s) this (these) region(s) being constituted:

by a nucleotide sequence coding for a messenger RNA (mRNA), this mRNA itself coding for a cinnamoyl CoA reductase (CCR) in plants, or a fragment of the nucleotide sequence mentioned above, this fragment coding for an mRNA, this mRNA itself coding for a fragment of a CCR in plants, this fragment of CCR having an enzymatic activity equivalent to that of the CCR mentioned above, or a nucleotide sequence derived from the nucleotide sequence mentioned above, or derived from the fragment mentioned above, in particular by mutation and/or addition, and/or suppression, and/or substitution of one or more nucleotides, this derived sequence coding for an mRNA, this mRNA itself coding for a derived protein having an enzymatic activity equivalent to that of the CCR mentioned above, or by a nucleotide sequence complementary to all or part of the nucleotide sequence coding for an mRNA, or of a fragment of this sequence, or of the sequence derived from these last-named, as defined above, this complementary sequence coding for an anti sense nucleotide sequence (also called anti sense mRNA) capable of hybridizing with one of the mRNAs mentioned above, for the transformation of plant cells with a view to obtaining transgenic plants within which the biosynthesis of lignins is regulated either in the sense of an increase, or in the sense of a reduction in the lignin levels produced, relative to the normal lignin levels produced in the plants.

By the expression "derived nucleotide sequence", in what has gone before and in what follows, is meant any sequence having at least about 50% of nucleotides homologous with those of the sequence from which it is derived.

By "derived protein", in what has gone before and in what follows, is meant any protein having at least about 50% of amino acids homologous with those of the protein from which it is derived.

Among the nucleotide sequences capable of being used as coding regions in the recombinant nucleotide sequences, there can principally be mentioned:

the nucleotide sequence represented by SEQ ID NO 1, coding for an mRNA, this mRNA itself coding for the CCR of eucalyptus represented by SEQ ID NO 2, the nucleotide sequence represented by SEQ ID NO 3, coding for an mRNA, this mRNA itself coding for the CCR of poplar represented by SEQ ID NO 4, the nucleotide sequence represented by SEQ ID NO 5, coding for an mRNA, this mRNA itself coding for the CCR of fescue represented by SEQ ID NO 6, the nucleotide sequence represented by SEQ ID NO 7, coding for an mRNA, this mRNA itself coding for the CCR of tobacco represented by SEQ ID NO 8, the nucleotide sequence complementary to that represented by SEQ ID NO 1, SEQ ID NO 3, SEQ ID NO 5 or SEQ ID NO 7, this complementary sequence coding for an anti sense mRNA capable of hybridizing with the mRNA coded by sequences SEQ ID NO 1, SEQ ID NO 3, SEQ ID NO 5 and SEQ ID NO 7 respectively, the nucleotide sequence derived from the sequence represented by SEQ ID NO 1, SEQ ID NO 3, SEQ ID NO 5 or SEQ ID NO 7, in particular by mutation and/or addition, and/or suppression, and/or substitution of one or more nucleotides, this derived sequence coding either for an mRNA itself coding for the CCR represented by SEQ ID NO 2, SEQ ID NO 4, SEQ ID NO 6 or SEQ ID NO 8 respectively, or for a protein derived from these last-named and having an enzymatic activity equivalent to that of said CCRs in plants, in particular the nucleotide sequence derived from sequence SEQ ID NO 1, and represented by SEQ ID NO 9, this latter coding for an mRNA, this mRNA itself coding for a protein represented by SEQ ID NO 10 derived from the eucalyptus CCR mentioned above, the nucleotide sequence derived from the complementary nucleotide sequence mentioned above, by mutation and/or addition, and/or suppression, and/or substitution of one or more nucleotides, this derived sequence coding for an anti sense mRNA capable of hybridizing with one of the mRNAs mentioned above.

A more particular subject of the present invention is any DNA sequence, characterized in that it contains as coding region:

the nucleotide sequence represented by SEQ ID NO 1, coding for an mRNA, this mRNA itself coding for the CCR represented by SEQ ID NO 2, or a fragment of the nucleotide sequence mentioned above, this fragment coding for a CCR fragment represented by SEQ ID NO 2, this CCR fragment having an enzymatic activity equivalent to that of the CCR mentioned above, or any nucleotide sequence derived from the sequence represented by SEQ ID NO 1 mentioned above, or from a fragment as described above of this sequence, in particular by mutation and/or addition, and/or suppression, and/or substitution of one or more nucleotides, this derived sequence coding for an mRNA itself coding for the CCR represented by SEQ ID NO 2, or for a protein derived from the latter and having an enzymatic activity equivalent to that of said CCR in plants, in particular the nucleotide sequence derived from the sequence SEQ ID NO 1, and represented by SEQ ID NO 9, this latter coding for an mRNA, this mRNA itself coding for a protein represented by SEQ ID NO 10 derived from the eucalyptus CCR mentioned above.

A more particular subject of the present invention is any DNA sequence, characterized in that it contains as coding region:

the nucleotide sequence represented by SEQ ID NO 3, coding for an mRNA, this mRNA itself coding for the CCR represented by SEQ ID NO 4, or a fragment of the nucleotide sequence mentioned above, this fragment coding for a CCR fragment represented by SEQ ID NO 4, this CCR fragment having an enzymatic activity equivalent to that of the CCR mentioned above, or any nucleotide sequence derived from the sequence represented by SEQ ID NO 3 mentioned above, or from a fragment as described above of this sequence, in particular by mutation and/or addition, and/or suppression, and/or substitution of one or more nucleotides, this derived sequence coding for an mRNA itself coding for the CCR represented by SEQ ID NO 4, or for a protein derived from the latter and having an enzymatic activity equivalent to that of the said CCR in plants.

A more particular subject of the present invention is any DNA sequence, characterized in that it contains as coding region:

the nucleotide sequence represented by SEQ ID NO 5, coding for an mRNA, this mRNA itself coding for the CCR represented by SEQ ID NO 6, or a fragment of the nucleotide sequence mentioned above, this fragment coding for a CCR fragment represented by SEQ ID NO 6, this CCR fragment having an enzymatic activity equivalent to that of the CCR mentioned above, or any nucleotide sequence derived from the sequence represented by SEQ ID NO 5 mentioned above, or from a fragment as described above of this sequence, in particular by mutation and/or addition, and/or suppression, and/or substitution of one or more nucleotides, this derived sequence coding for an mRNA itself coding for the CCR represented by SEQ ID NO 6, or for a protein derived from the latter and having an enzymatic activity equivalent to that of said CCR in plants.

A more particular subject of the present invention is any DNA sequence, characterized in that it contains as coding region:

the nucleotide sequence represented by SEQ ID NO 7, coding for an mRNA, this mRNA itself coding for the CCR represented by SEQ ID NO 8, or a fragment of the nucleotide sequence mentioned above, this fragment coding for a CCR fragment represented by SEQ ID NO 8, this CCR fragment having an enzymatic activity equivalent to that of the CCR mentioned above, or any nucleotide sequence derived from the sequence represented by SEQ ID NO 7 mentioned above, or from a fragment as described above of this sequence, in particular by mutation and/or addition, and/or suppression, and/or substitution of one or more nucleotides, this derived sequence coding for an mRNA itself coding for the CCR represented by SEQ ID NO 8, or for a protein derived from the latter and having an enzymatic activity equivalent to that of said CCR in plants.

By protein having an enzymatic activity equivalent to that of CCR present in plants, and more particularly CCRs represented by SEQ ID NO 2, SEQ ID NO 4, SEQ ID NO 6 and SEQ ID NO 8, is meant any protein having a CCR activity as measured according to the method of Luderitz and Grisebach in Eur. J. Biochem. (1981), 119: 115–127.

By way of illustration, this method is carried out by spectrophotometric measurement of the reducing activity of the protein (CCR or derivative), by monitoring the disappearance of cinnamoyl CoA at 366 nm. The reaction takes place at 30° C., for 2 to 10 minutes. The composition of the reaction medium is as follows: 100 mM phosphate buffer, pH 6.25, 0.1 mM NADPH, 70 $\mu$M Feruloyl CoA, 5 to 100 $\mu$l of enzymatic extract in a total volume of 500 $\mu$l.

Also a subject of the invention is any DNA sequence, characterized in that it contains as coding region:

the nucleotide sequence complementary to that represented by SEQ ID NO 1, this complementary sequence coding for an anti sense mRNA capable of hybridizing with the mRNA itself coding for the CCR represented by SEQ ID NO 2, namely the mRNA coded by the sequence represented by SEQ ID NO 1, or coded by a sequence derived from the latter, as defined above, or a fragment of the complementary sequence mentioned above, this sequence fragment coding for an anti sense mRNA capable of hybridizing with the mRNA itself coding for the CCR represented by SEQ ID NO 2, as defined above, or any nucleotide sequence derived from the complementary sequence mentioned above, or from a fragment of this complementary sequence as described above, in particular by mutation and/or addition, and/or suppression, and/or substitution of one or more nucleotides, this derived sequence coding for an anti sense mRNA capable of hybridizing with the mRNA mentioned above, in particular the sequence complementary to that represented by SEQ ID NO 9.

A more particular subject of the invention is any DNA sequence, characterized in that it contains as coding region:

the nucleotide sequence complementary to that represented by SEQ ID NO 3, this complementary sequence coding for an anti sense mRNA capable of hybridizing with the mRNA itself coding for the CCR represented by SEQ ID NO 4, namely the mRNA coded by the sequence represented by SEQ ID NO 3, or coded by a sequence derived from the latter, as defined above, or a fragment of the complementary sequence mentioned above, this sequence fragment coding for an anti sense mRNA capable of hybridizing with the mRNA itself coding for the CCR represented by SEQ ID NO 4, as defined above, or any nucleotide sequence derived from the complementary sequence mentioned above, or from a fragment of this complementary sequence as described above, in particular by mutation and/or addition, and/or suppression, and/or substitution of one or more nucleotides, this derived sequence coding for an anti sense mRNA capable of hybridizing with the mRNA mentioned above.

A more particular subject of the invention is any DNA sequence, characterized in that it contains as coding region:

the nucleotide sequence complementary to that represented by SEQ ID NO 5, this complementary sequence coding for an anti sense mRNA capable of hybridizing with the mRNA itself coding for the CCR represented by SEQ ID NO 6, namely the mRNA coded by the sequence represented by SEQ ID NO 5, or coded by a sequence derived from the latter, as defined above, or a fragment of the complementary sequence mentioned above, this sequence fragment coding for an anti sense mRNA capable of hybridizing with the mRNA itself coding for the CCR represented by SEQ ID NO 5, as defined above, or any nucleotide sequence derived from the complementary sequence mentioned above, or from a fragment of this complementary sequence as described above, in particular by mutation and/or addition, and/or suppression, and/or substitution of one or more nucleotides, this derived sequence coding for an anti sense mRNA capable of hybridizing with the mRNA mentioned above.

A more particular subject of the invention is any DNA sequence, characterized in that it contains as coding region:

the nucleotide sequence complementary to that represented by SEQ ID NO 7, this complementary sequence coding for an anti sense mRNA capable of hybridizing with the mRNA itself coding for the CCR represented by SEQ ID NO 8, namely the mRNA coded by the sequence represented by SEQ ID NO 7, or coded by a sequence derived from the latter, as defined above, or a fragment of the complementary sequence mentioned above, this sequence fragment coding for an anti sense mRNA capable of hybridizing with the mRNA itself coding for the CCR represented by SEQ ID NO 7, as defined above, or any nucleotide sequence derived from the complementary sequence mentioned above, or from a fragment of this complementary sequence as described above, in particular by mutation and/or addition, and/or suppression, and/or substitution of one or more nucleotides, this derived sequence coding for an anti sense mRNA capable of hybridizing with the mRNA mentioned above.

It will be understood that the sequences represented by SEQ ID NO 1, SEQ ID NO 3, SEQ ID NO 5, SEQ ID NO 7 and SEQ ID NO 9, the complementary sequences, the derived sequences and the fragments of sequences of the invention mentioned above, must be taken into consideration as being represented in the 5'→3' direction.

Thus, the first nucleotide of a complementary sequence in the 5'→3' direction as described above, is the complement of the last nucleotide of the sequence in the 5'→3' direction coding for a CCR (or fragment of CCR or derived protein), the second nucleotide of this complementary sequence is the complement of the next-to-last nucleotide of the sequence coding for a CCR, and so on, up to the last nucleotide of said complementary sequence which is the complement of the first nucleotide of the sequence coding for a CCR.

The mRNA coded by the complementary sequence mentioned above is such that, when this mRNA is represented in the 5'→3' direction, its first nucleotide corresponds to the last nucleotide of the sequence coding for a CCR, and therefore hybridizes with the last nucleotide of the mRNA coded by the latter, while its last nucleotide corresponds to the first nucleotide of the sequence coding for a CCR, and therefore hybridizes with the first nucleotide of the mRNA coded by the latter.

In this way, by anti sense mRNA is meant in what has gone before and in what follows, any mRNA coded by foresaid complementary sequence and represented in the reverse direction (3'→5') to the direction in which the mRNA coded by the sequence coding for a CCR (or fragment of CCR or derived protein) is represented, this last-named mRNA still being called (5'→3') direction mRNA.

The term anti sense RNA therefore refers to an RNA sequence complementary to the sequence of bases of the messenger RNA, the term complementary having to be understood in this way that each base (or a majority of bases) of the anti sense sequence (read in the 3'→5' direction) is capable of pairing with the corresponding bases (G with C, A with U) of the messenger RNA (sequence read in the 5'→3' direction).

The anti sense RNA strategy, within the scope of the present invention, is a molecular approach particularly suitable to the objective of modifying the lignin levels of plants. The anti sense RNA is an RNA produced by the transcription of a non-coding DNA strand (non sense strand).

This anti sense strategy is more particularly described in the European Patent No. 240 208.

It is thought that the inhibition of the synthesis of a protein according to the anti sense strategy, of CCR in the present case, is the consequence of the formation of a duplex between the two complementary RNAs (sense and anti sense) thus inhibiting the production of the protein. However the mechanism remains unclear. The RNA—RNA complex may interfere either with a subsequent transcription, or with processing, transport or translation or even lead to degradation of the mRNA.

A combination of these effects is also possible.

The invention also relates to any mRNA coded by a DNA sequence according to the invention, and more particularly:

the mRNA coded by the DNA sequence represented by SEQ ID NO 1, or coded by a fragment or a derived sequence as defined above, said mRNA being in turn capable of coding for the CCR present in eucalyptus, as represented by SEQ ID NO 2, or for a fragment of this CCR or a derived protein as defined above, in particular for the protein represented by SEQ ID NO 10, the mRNA coded by the DNA sequence represented by SEQ ID NO 3, or coded by a fragment or a derived sequence as defined above, said mRNA being in turn capable of coding for the CCR present in poplar, as represented by SEQ ID NO 4, or for a fragment of this CCR or a derived protein as defined above, the mRNA coded by the DNA sequence represented by SEQ ID NO 5, or coded by a fragment or a derived sequence as defined above, said mRNA being in turn capable of coding for the CCR present in fescue, as represented by SEQ ID NO 6, or for a fragment of this CCR or a derived protein as defined above, the mRNA coded by the DNA sequence represented by SEQ ID NO 7, or coded by a fragment or a derived sequence as defined above, said mRNA being in turn capable of coding for the CCR present in tobacco, as represented by SEQ ID NO 8, or for a fragment of this CCR or a derived protein as defined above.

Also a subject of the invention is any anti sense mRNA, as defined above, characterized in that it contains complementary nucleotides of all or only part of the nucleotides constituting an mRNA as described above according to the invention, said anti sense mRNA being capable of hybridizing (or pairing) with the latter.

As such, a more particular subject of the invention is the anti sense mRNAs coded by DNA sequences according to the invention, containing at least one region of 50 bases homologous with those of a region of complementary sequences of the above-mentioned DNA sequences of the invention.

There is no upper size limit for the DNA sequences coding for an anti sense RNA according to the invention; they can be as long as those of the messenger normally produced in these cells, even as long as the genomic DNA sequence coding for the mRNA of the CCR.

Advantageously, such DNA sequences coding for an anti sense RNA according to the invention, contain between about 100 and about 1000 base pairs.

A more particular subject of the invention is any anti sense sequence containing one (or more) anti sense mRNAs as described above, or fragment(s) of this (these) anti sense mRNA(s), and one (or more) sequence(s) corresponding to one (or more) catalytic domain(s) for a ribozyme.

As such, a more particular subject of the invention is any anti sense sequence as described above, containing the catalytic domain for a ribozyme flanked on either side by arms of about 8 complementary bases of sequences bordering a GUX unit (X representing C, U or A) contained in one of the mRNAs of the invention described above (also called target RNAs) (Haseloff J., and Gerlach W. L., 1988, Nature, 334: 585–591).

The invention also relates to any DNA sequence capable of coding for an anti sense sequence as described above containing at least one catalytic domain for a ribozyme related to one or more anti sense mRNAs of the invention, or anti sense mRNA fragments (advantageously fragments of about 8 bases as described above).

A more particular subject of the invention is also any anti sense sequence containing:

any anti sense mRNA, as described above, characterized in that it is coded by the nucleotide sequence complementary to that represented by SEQ ID NO 1, said anti sense mRNA being capable of hybridizing with the mRNA coded by the DNA sequence represented by SEQ ID NO 1, any anti sense mRNA, as described above, characterized in that it is coded by the nucleotide sequence complementary to that represented by SEQ ID NO 3, said anti sense mRNA being capable of hybridizing with the mRNA coded by the DNA sequence represented by SEQ ID NO 3, any anti sense mRNA, as described above, characterized in that it is coded by the nucleotide sequence complementary to that represented by SEQ ID NO 5, said anti sense mRNA being capable of hybridizing with the mRNA coded by the DNA sequence represented by SEQ ID NO 5, any anti sense mRNA, as described above, characterized in that it is coded by the nucleotide sequence complementary to that represented by SEQ ID NO 7, said anti sense mRNA being capable of hybridizing with the mRNA coded by the DNA sequence represented by SEQ ID NO 7, any anti sense mRNA, as described above, characterized in that it is coded by the nucleotide sequence complementary to that represented by SEQ ID NO 9, said anti sense mRNA being capable of hybridizing with the mRNA coded by the DNA sequence represented by SEQ ID NO 9.

The invention also relates to the recombinant polypeptides coded the DNA sequences of the invention, said recombinant polypeptides having an enzymatic activity equivalent to that of the CCRs in plants, and more particularly the recombinant CCRs coded by the sequences represented by SEQ ID NO 1, SEQ ID NO 3, SEQ ID NO 5 and SEQ ID NO 7, or by sequences derived from these last-named according to the invention, in particular by SEQ ID NO 9.

A more particular subject of the invention is the recombinant polypeptides, and in particular the recombinant CCRs, as obtained by transformation of plant cells by integrating in a stable fashion a recombinant nucleotide sequence as defined above, containing a DNA sequence according to the invention, in their genome, in particular using a vector as described hereafter.

By the expression "recombinant polypeptides", one must understand any molecule having a polypeptide chain capable of being produced by genetic engineering, by means of a transcription phase of the DNA of the corresponding gene, which leads to the obtaining of RNA which is then transformed into mRNA (by suppression of the introns), the latter then being translated by the ribosomes, in the form of proteins, all of this being carried out under the control of appropriate regulation elements inside a host cell. Consequently, the expression "recombinant polypeptides" used does not exclude the possibility that said polypeptides contain other groups, such as glycosylated groups.

Of course, the term "recombinant" indicates that the polypeptide was produced by genetic engineering, as it results from the expression, in an appropriate host cell, of the corresponding nucleotide sequence which has been introduced beforehand into an expression vector used to transform said host cell. However, this term "recombinant" does not exclude the possibility that the polypeptide was produced by a different process, for example by standard chemical synthesis according to known methods used for the synthesis of proteins, or by proteolytic cleavage of much larger molecules.

More particularly the invention relates to CCR such as is present in eucalyptus cells and represented by SEQ ID NO 2, the CCR such as is present in poplar cells and represented by SEQ ID NO 4, CCR such as is present in tall fescue cells and represented by SEQ ID NO 6, or CCR such as is present in tobacco cells and represented by SEQ ID NO 8, or any protein derived from these last-named, in particular by addition, and/or suppression, and/or substitution of one or more amino acids, in particular the protein derived from eucalyptus CCR and represented by SEQ ID NO 10, or any fragment originating from said CCRs or from their derived sequences, said fragments and derived sequences being capable of having an enzymatic activity equivalent to that of the CCRs mentioned above.

Also a subject of the invention is the nucleotide sequences coding for the CCR represented by SEQ ID NO 2, SEQ ID NO 4, SEQ ID NO 6, SEQ ID NO 8 or SEQ ID NO 10, or any derived sequence or fragment of these last-named, as defined above, said nucleotide sequences being characterized in that they correspond to all or part of the sequences represented by SEQ ID NO 1, SEQ ID NO 3, SEQ ID NO 5, SEQ ID NO 7 or SEQ ID NO 9 respectively, or to any sequence derived from these last-named by degeneration of the genetic code, and nevertheless being capable of coding for the CCRs or derived sequence or fragment of these last-named, as defined above.

A subject of the invention is also the complexes formed between the anti sense mRNAs, as described above, and the mRNAs according to the invention, capable of coding for all or part of a CCR in plants.

A more particular subject of the invention is the complex formed between the mRNA coded by the sequence SEQ ID NO 1 and the anti sense mRNA coded by the sequence complementary to the sequence SEQ ID NO 1, the mRNA coded by the sequence SEQ ID NO 3 and the anti sense mRNA coded by the sequence complementary to the sequence SEQ ID NO 3, the mRNA coded by the sequence SEQ ID NO 5 and the anti sense mRNA coded by the sequence complementary to the sequence SEQ ID NO 5, the mRNA coded by the sequence SEQ ID NO 7 and the anti sense mRNA coded by the sequence complementary to the sequence SEQ ID NO 7, the mRNA coded by the sequence SEQ ID NO 9 and the anti sense mRNA coded by the sequence complementary to SEQ ID NO 9.

Also a subject of the invention is any recombinant nucleotide sequence containing one (or more) coding region(s), this (these) coding region(s) being constituted:

by a nucleotide sequence coding for an mRNA, this mRNA itself coding for a CCR in plants, or a fragment of the nucleotide sequence mentioned above, this fragment coding for an mRNA, this mRNA itself coding for a fragment of a CCR in plants, this fragment of CCR having an enzymatic activity equivalent to that of the CCR mentioned above, or a nucleotide sequence derived from the nucleotide sequence mentioned above, or derived from the fragment mentioned above, in particular by mutation and/or addition, and/or suppression, and/or substitution of one or more nucleotides, this derived sequence coding for an mRNA, this mRNA itself coding for a derived protein having an enzymatic activity equivalent to that of the CCR mentioned above, or by a nucleotide sequence complementary to all or part of the nucleotide sequence coding for an mRNA, or of the fragment of this sequence, or of the sequence derived from these last-named, as defined above, this complementary sequence coding for an anti sense mRNA capable of hybridizing with one of the mRNAs mentioned above.

A more particular subject of the invention is any recombinant nucleotide sequence (or recombinant DNA), characterized in that it contains at least one DNA sequence according to the invention, chosen from those described above, said DNA sequence being inserted in a heterologous sequence.

More particularly the invention relates to any recombinant nucleotide sequence as described above, containing, as coding region, the nucleotide sequence represented by SEQ ID NO 1, or by SEQ ID NO 3, or by SEQ ID NO 5, or by SEQ ID NO 7, or any fragment or a nucleotide sequence derived from the last-named, as defined above, said nucleotide sequences or said fragment being inserted in a heterologous sequence, and being capable of coding for the CCR represented by SEQ ID NO 2, or by SEQ ID NO 4, or by SEQ ID NO 6 or by SEQ ID NO 8 respectively, or for a fragment of these CCRs, or for a protein derived from these last-named, as defined above.

More particularly still the invention relates to any recombinant nucleotide sequence containing, as coding region, a nucleotide sequence complementary to that represented by SEQ ID NO 1, or by SEQ ID NO 3, or by SEQ ID NO 5, or by SEQ ID NO 7, or any fragment or any nucleotide sequence derived from this complementary sequence, as defined above, said complementary sequences or said fragment being inserted in a heterologous sequence, and being capable of coding for an anti sense mRNA capable of hybridizing with all or part of the mRNA coding for a CCR in plants, and more particularly with all or part of the mRNA coding for the CCR represented by SEQ ID NO 2, or by SEQ ID NO 4, or by SEQ ID NO 6, or by SEQ ID NO 8 respectively.

The recombinant DNAs according to the invention are further characterized in that they contain the elements necessary to regulate the expression of the nucleotide sequence coding for a CCR, or of its complementary sequence coding for an anti sense mRNA according to the invention, in particular a promoter and a terminator of the transcription of these sequences.

Among the different promoters which are capable of being used in the construction of recombinant DNAs according to the invention, there can be mentioned:

the endogenous promoter controlling the expression of CCR in a plant, in particular the promoter situated upstream from the sequence represented by SEQ ID NO 1 in eucalyptus, or constitutive-type strong-expression promoters, examples: $^{35}$S CAMV (described in Benfey et al. (1990), EMBO J., 9 (6), 1677–1684), EF1alpha (promoter of a gene with an elongation factor in the protein synthesis described by Curie et al. (1991), Nucl. Acids Res., 19, 1305–1310), promoters of specific type for particular expression in individual tissues, examples: CAD promoter (described by Feuillet C. (1993), University of Toulouse III Thesis), promoter GRP 1–8 (described by Keller and Baumgartner, (1991), Plant Cell., 3, 1051–1061) for expression in specific vascular tissues.

The invention also relates to any recombinant nucleotide sequence as described above, and also containing as coding region at least one nucleotide sequence coding for all or part of an mRNA itself coding for an enzyme other than CCR, which is implicated in a stage of the biosynthesis of lignins in plants, in particular the mRNA coding for cinnamyl alcohol dehydrogenase (CAD), or also containing as coding region at least one nucleotide sequence coding for all or part of an anti sense mRNA capable of hybridizing with the mRNA mentioned above, in particular with the mRNA coding for CAD.

The recombinant nucleotide sequences of the invention mentioned above are advantageously obtained from vectors in which the DNA sequences coding for an enzyme necessary for the biosynthesis of lignins in plants are inserted.

By way of illustration, a more particular subject of the invention is the vector called pEUCCR, containing the sequence represented by SEQ ID NO 1 cloned in the Bluescript vector, and deposited in culture in cells of *E. Coli* DH5alpha at the Collection Nationale de Culture de Microorganisms (CNCM) at the Institut Pasteur in Paris (France), on Mar. 17, 1994 under No. I-1405.

The vectors mentioned above are digested using appropriate restriction enzymes in order to recover said DNA sequences which are inserted in them.

The last-named are then inserted downstream from an appropriate promoter, and upstream from an appropriate terminator for the expression, in the recombinant DNAs according to the invention.

More particularly a subject of the invention is the recombinant DNAs containing the sequence represented by SEQ ID NO 1, coding for the mRNA itself coding for the CCR represented by SEQ ID NO 2, as obtained by digestion of the pEUCCR vector mentioned above, recovery of the DNA sequence of the invention and insertion of the latter in the 5'→3' direction, in a heterologous DNA sequence containing a promoter and a terminator of the expression of said sequence.

A more particular subject of the invention is also the recombinant DNAs containing the sequence complementary to the sequence SEQ ID NO 1, coding for an anti sense mRNA capable of hybridizing with the mRNA coding for the CCR represented by SEQ ID NO 2, as obtained by digestion of the pEUCCR vector mentioned above, recovery of the DNA sequence of the invention, and insertion of the latter in the reverse direction, that is to say in the 3'→5' direction, in a heterologous DNA sequence containing a promoter and a terminator of the expression of the complementary sequence.

As an example of a terminator which can be used in such constructions, there can be mentioned the 3' end of the gene of the nopaline synthase of *Agrobacterium tumefaciens*.

Therefore, in a general manner, the recombinant nucleotide sequences according to the invention, containing a DNA sequence coding for a CCR (or a CCR fragment or derived protein), and/or other enzymes necessary for the biosynthesis of lignins, are obtained by recovery of said DNA sequence from the vectors mentioned above, and insertion of this sequence in the heterologous sequence, while the recombinant nucleotide sequences containing a DNA sequence coding for an anti sense mRNA according to the invention, are obtained by recovery of the DNA sequence mentioned above and insertion of the latter in the reverse direction in said heterologous sequence.

By way of illustration, there can be used all or part of the complementary DNA (cDNA) represented by SEQ ID NO 1, SEQ ID NO 3, SEQ ID NO 5, SEQ ID NO 7 or SEQ ID NO 9, for the construction of the recombinant DNAs mentioned above, or all or part of the genomic clone corresponding to a CCR (which corresponds to the cDNAs mentioned above + possible introns). This genomic clone can be obtained using the cDNAs as probes to screen a gene library, the latter being itself obtained according to the method described by Sambrook, Fritsch and Maniatis, Molecular Cloning Laboratory Manual, Cold Spring Harbour Laboratory Press, 1989.

A subject of the invention is also any recombinant vector, which can be used for the transformation of plants, characterized in that it contains a recombinant nucleotide sequence chosen from those described above, according to the invention, integrated in one of the sites of its genome which is not essential for its replication.

Among the recombinant vectors mentioned above which can be used for the transformation of plants, there can be mentioned: the binary vectors derived from pBIN 19 (Bevan et al., (1984), Nucl. Acids Res., 12(22), 8711–8721).

Examples of the construction of recombinant vectors according to the invention are described in the detailed description of the invention which follows.

Also a subject of the present invention is a process for the regulation of the biosynthesis of lignins in plants, either by reducing, or by increasing the quantities of lignin produced, relative to the normal quantities of lignins produced in these plants, said process containing a transformation stage of the cells of these plants using a vector containing:

a nucleotide sequence coding for an mRNA, this mRNA itself coding for a CCR in plants, or a fragment of the nucleotide sequence mentioned above, this fragment coding for an mRNA, this mRNA itself coding for a fragment of a CCR in the plants, this CCR fragment having an enzymatic activity equivalent to that of the CCR mentioned above, or a nucleotide sequence derived from the nucleotide sequence mentioned above, or derived from the fragment mentioned above, in particular by mutation and/or addition, and/or suppression, and/or substitution of one or more nucleotides, this derived sequence coding for an mRNA, this mRNA itself coding for a derived protein having an enzymatic activity equivalent to that of the CCR mentioned above, or a nucleotide sequence complementary to all or part of the nucleotide sequence coding for an mRNA, or of a fragment of this sequence, or of the sequence derived from these last-named, as defined above, this complementary sequence coding for an anti sense mRNA capable of hybridizing with one of the mRNAs mentioned above, said transformation being carried out in particular using a vector as described above.

A more particular subject of the invention is a process for the reduction of the quantity of lignins produced by biosynthesis in plants, this process being carried out by the transformation of the genome of these plants, by incorporating in it:

at least one DNA sequence according to the invention as described above, coding for an anti sense mRNA capable of hybridizing with all or part of the mRNA coding for the CCR represented by SEQ ID NO 2, SEQ ID NO 4, SEQ ID NO 6 or SEQ ID NO 8, or for a protein derived from these last-named as defined above, in particular for the protein represented by SEQ ID NO 10, and, if appropriate, at least one DNA sequence coding for an anti sense mRNA capable of hybridizing with an mRNA coding for an enzyme other than CCR, which is implicated in a stage of the biosynthesis of lignins in plants, in particular the mRNA coding for CAD, said transformation being carried out:

either using a recombinant vector as described above, containing a DNA sequence coding for an anti sense mRNA capable of hybridizing with the mRNA coding for CCR or for a derived protein, as defined above, and if appropriate, containing one or more DNA sequence (s) coding for an anti sense mRNA capable of hybridizing with an mRNA coding for an enzyme other than CCR as defined above, or using several recombinant vectors at least one of which contains a DNA sequence coding for an anti sense mRNA capable of hybridizing with the mRNA coding for CCR or for a derived protein, as defined above, while the other recombinant vector(s) contain(s) a DNA sequence coding for an anti sense mRNA capable of hybridizing with an mRNA coding for an enzyme other than CCR, as defined above.

Another process for reducing the quantity of lignins produced by biosynthesis in plants, is that carried out by transformation of the genome of these plants, by incorporating in it:

at least one DNA sequence according to the invention represented by SEQ ID NO 1, SEQ ID NO 3, SEQ ID NO 5 or SEQ ID NO 7, or a fragment or a sequence derived from the latter, as defined above, in particular the sequence represented by SEQ ID NO 9, and, if appropriate, at least one DNA sequence coding for all or part of an enzyme other than CCR, which is implicated in a stage of the biosynthesis of lignins in plants, in particular a DNA sequence coding for all or part of CAD, said transformation being carried out:

either using a recombinant vector as described above, containing the DNA sequence according to the invention mentioned above, or a fragment or a sequence derived from the latter, as defined above, and, if appropriate, containing one or more DNA sequence(s) coding for all or part of an enzyme other than CCR, as defined above, or using several recombinant vectors at least one of which contains a DNA sequence according to the invention mentioned above, or a fragment or a sequence derived from the latter, as defined above, while the other recombinant vector(s) contain(s) a DNA sequence coding for all or part of an enzyme other than CCR as defined above.

This last method requires a co-suppression mechanism. Co-suppression was observed when copies of the endogenous gene were introduced into the genome. Whilst the co-suppression mechanism is at present unknown, one of the most frequently accepted hypotheses is that the negative regulation of the expression of the gene may result from the production a small quantity of anti sense RNA derived from a transgene through a reading of the "wrong" strand of the transgene (Grierson et al., Trends Biotech., 9: 122–123).

A subject of the invention is also a process for the reduction of the quantity of lignins produced by biosynthesis in plants, this process being carried out by transformation of the genome of these plants by incorporating in it a DNA sequence as described above according to the invention, coding for an anti sense sequence containing one or (more) catalytic domain(s) for a ribozyme related to one (more) anti sense mRNAs, or anti sense mRNA fragments of the invention, said transformation being carried out using a recombinant vector containing a recombinant nucleotide sequence according to the invention itself containing the DNA sequence mentioned above.

It is important to note that the methods mentioned above allow transformed plants to be produced having different level of reduction in the CCR activity (according to the level of insertion of the DNA sequence coding for the anti sense mRNA, the number of copies of this DNA sequence integrated in the genome . . . ) and therefore the lignin levels.

The choice of transformants will therefore allow a controlled modulation of the lignin levels compatible with a normal development of the plant.

In a general manner, if one considers that the normal average level of lignins of a plant varies between about 15% and about 35% by weight of dry matter, the reduction in the level of lignins resulting from the implementation of one of the processes mentioned above, is advantageously such that the plants transformed in this way have an average level of lignins varying between about 10% and about 30%, or also between about 12% and about 32%.

By way of illustration, the lignin level of a plant can be measured according to a variant of the method of Johnson et al., (1961), T.A.P.P.I., 44, 793–798, which is described in detail in Alibert and Boudet (1979), Physiol., Veg., 17 (1), 67–74, and the principal stages of which are the following: after obtaining a benzene alcohol powder containing lignins of plant material, the lignins are solubilized with acetyl bromide and analyzed as a function of their absorption in the ultraviolet.

A more particular subject of the invention is the use of the processes mentioned above for the reduction of lignin levels in plants, for obtaining genetically-transformed fodder crops, having lignin levels which are reduced relative to the normal lignin levels in these plants, and in this way the digestibility of which is improved relative to the same untransformed plants.

Among the main fodder crops capable of being transformed within the scope of the present invention, there can be mentioned: alfalfa, fescue, maize used for silage, etc . . . .

The invention also relates to the use of the processes mentioned above for the reduction of the lignin levels in plants, for obtaining genetically-transformed plants, and more particularly trees, having lignin levels which are reduced relative to the normal lignin levels in these plants, these plants or trees being particularly advantageous for use within the scope of the production of paper pulp.

A third potential field of use of the processes mentioned above for the negative regulation of the expression of the CCR gene relates to the stimulation of the growth of transformed plants. Various arguments emphasize (Sauter and Kende, 1992, Plant and Cell Physiology, 33 (8):1089), that early and rapid lignification acts as a brake on cell enlargement and therefore on the growth of plants. Thus the implementation of the processes mentioned above is capable of allowing plants transformed in this way with reduced lignification better growth and therefore better yields.

The invention also relates to a process for increasing the quantity of lignins produced by biosynthesis in plants, this process being carried out by transformation of the genome of these plants, by incorporating in it:

at least one DNA sequence according to the invention represented by SEQ ID NO 1, SEQ ID NO 3, SEQ ID NO 5 or SEQ ID NO 7, or a fragment or a sequence derived from the latter, as defined above, in particular the sequence represented by SEQ ID NO 9, and, if appropriate, at least one DNA sequence coding for all or part of an enzyme other than CCR, which is implicated in a stage of the biosynthesis of lignins in plants, in particular a DNA sequence coding for all or part of CAD, said transformation being carried out:

either using a recombinant vector as described above, containing the DNA sequence according to the invention mentioned above, or a fragment or a sequence derived from the latter, as defined above, and, if appropriate, containing one or more DNA sequence(s) coding for all or part of an enzyme other than CCR, as defined above, or using several recombinant vectors at least one of which contains a DNA sequence according to the invention mentioned above, or a fragment or a sequence derived from the latter, as defined above, while the other recombinant vector(s) contain(s) a DNA sequence coding for all or part of an enzyme other than CCR as defined above.

In a general manner, still if one considers that the normal average lignin level of a plant varies between about 15% and about 35% by weight of dry matter, the increase in the lignin level resulting from the implementation of the process mentioned above, is advantageously such that the plants transformed in this way have an average lignin level varying between about 20% and about 40%, between about 18% and about 38%.

A more particular subject of the invention is the use of the process mentioned above for the increase in lignin levels in plants (also called process for the overexpression of the CCR gene), to obtain genetically transformed plants, having increased lignin levels relative to the normal lignin levels in plants, and of which the resistance properties to environmental attacks, in particular to parasite attacks, are thus improved relative to the same untransformed plants. It is particularly advantageous in this last case to use in combination with the CCR gene, or a derived sequence, in the vectors mentioned above, specific promoters particularly expressed in the surface tissues and/or in response to injury.

Furthermore, the invention also relates to the use of the process mentioned above for the overexpression of the CCR gene, to improve the growth of plants genetically transformed in this way, in particular in certain fields such as horticulture or arboriculture, where the obtaining of small plants is desired.

Finally, the benzene rings in lignin have higher intrinsic energy than the aliphatic chains of the glucose residues of cellulose. Therefore, the increase in the proportion of lignins in plants used as fuels, according to the process of the invention mentioned above, allows improvement of the potential energy of these fuel plants transformed in this way.

In the two cases of negative regulation or overexpression of CCR, it is quite conceivable that the modulation of this activity has repercussions on the lignin levels of the transformed plants. In fact, the CCR, the activity level of which is very low in the plant, appears to constitute the regulating enzyme for the synthesis of lignins.

Regarding the transformation techniques used for the implementation of one of the process described above of the invention, the following techniques will be advantageously used:

A) The technique of transformation using plasmid Ti of *Agrobacterium tumefaciens* described by Bevan (1984) Nucleic Acid Research, 12: 8711–8721. It essentially uses the co-culture method, and brings into play a co-transformation with a selection gene in order to be able to locate the transformants.

It is particularly applicable to dicotyledons, ex.: tobacco, alfalfa, oilseed rape.

B) The technique of direct transfer of genes by biological ballistics described in detail by (Zumbrum et al., 1989, Technique 1, 204–216; Sanford et al., 1991, Technique 3, 3–16).

This technique involves the combination of the recombinant DNA according to the invention with microparticles of gold or tungsten which are propelled using a gene gun onto the tissue to be transformed. It will be particularly applied to the transformation of refractory species to agrobacteria.

In the two cases mentioned above, verification of the presence of the recombinant DNA according to the invention will be carried out using southern type hybridization and genetic amplification (polymerase chain reaction) tests, using oligonucleotide probes and primers originating in particular from the sequence SEQ ID NO 1, SEQ ID NO 3, SEQ ID NO 5, SEQ ID NO 7 or SEQ ID NO 9.

The invention also relates to the plant cells transformed by a vector according to the invention, in particular using the techniques described above, and containing a DNA sequence according to the invention integrated in a stable fashion in their genome.

Also a subject of the invention is the transformed plants as obtained by culturing the transformed cells mentioned above.

The transformed plants can then be propagated by sexual route or by vegetative route in vitro or in natura.

A subject of the invention is also the fragments of plants, in particular fruits, seeds, pollen, transformed by incorporation in their genome of a DNA sequence according to the invention, using the recombinant vectors mentioned above.

The invention also relates to the antibodies directed against the recombinant polypeptides of the invention, and more particularly those directed against the recombinant CCRs mentioned above.

Such antibodies can be obtained by the immunization of an animal with these polypeptides followed by recovery of the antibodies formed.

It will be understood that this production is not limited to polyclonal antibodies.

It also applies to any monoclonal antibody produced by any hybridoma capable of being formed, by standard methods, from the splenic cells of an animal, in particular mice or rats, immunized against one of the purified polypeptides of the invention on the one hand, and cells of an appropriate myeloma on the other hand, and of being selected, by its capacity to produce monoclonal antibodies recognising the polypeptide mentioned above initially used for the immunization of the animals.

Also a subject of the invention is the use of antibodies mentioned above directed against the recombinant polypeptides of the invention, for the implementation of a detection or analysis method of CCRs in plants, starting from samples taken from these last-named.

More details of the invention will be given in the description which follows for the obtaining of CCR in purified form from the eucalyptus, and of the cDNA coding for CCR of the eucalyptus, poplar, tall fescue and tobacco.

EXAMPLES

Although the invention has been described in conjunction with specific embodiments, it is evident that many alternatives and variations will be apparent to those skilled in the art in light of the foregoing description. Accordingly, the invention is intended to embrace all of the alternatives and variations that fall within the spirit and scope of the appended claims.

All references cited through the disclosure are hereby incorporated by reference.

A) Obtaining purified eucalyptus CCR and the cDNA coding for a eucalyptus CCR.

I Purification of eucalyptus CCR.

CCR has been the subject of a number of very restricted studies. Among the few publications relating to it, there can be mentioned:

Wengenmayer H., Ebel J., Grisebach H., 1976—Enzymatic synthesis of lignin precursors, purification and properties of a cinnamoyl CoA: NaDPH reductase from cell suspension cultures from soyabean (Glycine max), Eur. J. Biochem., 65: 529–536.

Luderitz T., Grisebach H., 1981—Enzymatic synthesis of lignin precursors, comparison of cinnamoyl: CoA reductase and cinnamyl alcohol dehydrogenase: NADP dehydrogenase from spruce (*Picea abies L.*) and soyabean (*Glycine max L.*), Eur. J. Biochem., 119: 115–127.

Sarni F., Grand C., Boudet A. M., 1984—Purification and properties of cinnamoyl: CoA reductase and cinnamyl alcohol dehydrogenase from poplar stems (*Populus x euramericana*). Eur. J. Biochem., 139: 259–265.

The work described hereafter has contributed to the definition of a protocol for the original, simple and rapid purification of eucalyptus CCR. This protocol is also more effective than those described previously in the literature. In fact, it has allowed for the first time, quantities of homogeneous purified enzyme to be obtained which are sufficient to obtain internal peptide sequences and eventually lead to the cloning of the corresponding cDNA.

All the purification stages of the CCR were carried out at 4° C.

1. Obtaining a crude extract of eucalyptus xylem.

The plant matter was obtained by "scraping" a xylem-enriched tissue fraction from branches of 5-year-old *Eucalyptus gunnii*.

300 g of xylem frozen beforehand in liquid nitrogen was reduced to powder using a coffee mill. The homogenate thus obtained was homogenized in one liter of extraction buffer (100 mM Tris-HCl pH 7.6, 2% PEG 6000, 5 mM DTT, 2% PVPP), filtered through two thicknesses of Miracloth, and brought to 30% saturation with ammonium sulphate. After centrifuging for 30 minutes at 15000× g, the pellet obtained is resuspended in 60 ml of buffer 1 [20 mM Tris-HCl pH 7.5, 5 mM DTT (dithiothreitol), 5% ethylene glycol]. The extract thus obtained is "clarified" by a 15 minute centrifugation at 10000× g, then desalted by passage through a Sephadex G25 equilibrated with buffer 1.

2. Affinity chromatography on Red Sepharose.

The crude desalted extract is applied to a "Red Sepharose" affinity column (1.5×19 cm, Pharmacia), equilibrated with buffer 1. After an initial rinsing of the column with 50 ml of buffer 1, the proteins are eluted with a linear gradient of Tris from 20 mM to 1.5 M Tris-HCl pH 7.5, containing 5 mM DTT, 5% ethylene glycol. The total volume of the gradient is 200 ml and the flow rate is 36 ml/hr. The fractions having a CCR activity are collected and desalted by passage through a Sephadex G25 column, equilibrated with buffer 1.

3. Anion exchange chromatography on MonoQ.

The fractions collected and desalted in this way are chromatographed on a MonoQ anion exchange column (HR 5/5, Pharmacia). Elution of the proteins is carried out by the application of a linear gradient of 20 to 300 mM Tris-HCl pH 7.5, containing 5% ethylene glycol and 5 mM DTT. The total volume of the gradient is 50 ml and the flow rate is 1 ml/min. As with the previous stage, the fractions containing the active CCR enzyme are collected and desalted, but in this case the equilibration buffer for the Sephadex G25 columns is a 20 mM phosphate buffer, pH 7.6, containing 5 mM DTT (buffer 2).

4. Affinity chromatography on "Mimetic Red".

The group of CCR fractions obtained in this way is applied to a Mimetic Red 2 A6XL column (ACL, Cambridge). The column is washed beforehand with 30 ml of buffer 2 containing 8 mM of NAD. The object of this washing is to eliminate enzymes functioning specifically with NAD as a co-factor, such as the malate dehydrogenase which copurifies with the CCR in the previous stages. The specific elution of CCR is obtained by application of a gradient (15 ml) of NADP 0–8 mM in buffer 2. The fractions containing the pure and active CCR are stored at −80° C. after the addition of a stabiliser (ethylene glycol at a final concentration of 5%).

The purified enzyme thus obtained has a specific activity of 451 nKat/mg of protein, using feruloyl CoA as substrate. The yield obtained (36 µg of pure protein for 300 g of initial plant matter) does not reflect the proportion of CCR in planta, in fact due to a major concern to eliminate the maximum amount of contaminants at each purification stage, only the fractions having a very strong CCR activity are treated in the following stage. The purification factor obtained with this protocol is 282.

II Characterisation of the CCR.

The eucalyptus CCR is a monomer of 38 kD as witnessed by the convergent results obtained for the size of the native enzyme by exclusion chromatography on Superose 6 (Pharmacia), and for the size of the monomer sub-unit on denaturing electrophoresis gel. The isoelectric point, estimated by chromatography on MonoP (Pharmacia) is close to 7.

Research into the pH and optimum buffer shows that the measurement of CCR activity as it was initially described (Luderitz and Grisebach, 1981), is perfectly adapted to the measurement of the eucalyptus CCR activity (100 mM phosphate buffer, pH 6.25).

The purity of the CCR, present in the state of a single band on one-dimensional electrophoresis gel (SDS PAGE) was confirmed by the obtaining of a single spot after two-dimensional electrophoresis and staining with silver salts.

III Obtaining the cDNA coding for eucalyptus CCR

In order to avoid a possible problem of non-detectable residual contamination, the pure enzyme was subjected to a preparative electrophoresis under semi-denaturing conditions and digested in situ in the gel. The digestion was carried out using endolysine C which specifically cuts the proteins after the lysine residues, allowing relatively long peptides to be obtained. The peptides resulting from the digestion were separated by reversed phase HPLC and sone of them were sequenced using a protein microsequencer (Applied Biosystems 470). The sequences of these internal peptides are shown below:

```
peptide 8      (a) Asn-Trp-Tyr-Cys-Tyr-Gly-Lys
               (b) His-Leu-Pro-Val-Pro-X-Pro-Pro-Glu-Asp
                   Ser-Val-Arg
            X representing any amino acid peptide 10  Thr-Tyr-Ala-Asn-Ser-Val-Gln-Ala-Tyr-Val-His-
            Val-Lys peptide 13  Gly-Cys-Asp-Gly-Val-Val-His-Thr-Ala-Ser-Pro-
            Val-Thr-Asp-Asp peptide 17 Leu-Arg-Asp-Leu-Gly-Leu-Glu-Phe-Thr-Pro-Val-
            Lys peptide 18  Gly-Asp-Leu-Met-Asp-Tyr-Gly-Ser-Leu-Glu-Glu-
            Ala-Ile-Lys
```

The cDNA coding for the CCR was obtained by screening using oligonucleotides from a cDNA library constructed in the λZAPII phage (commercially available vector, Stratagène) from messenger extracts of xylem of *Eucalyptus gunnii*. 600,000 phages were screened using a group of degenerate oligonucleotides labelled at the 3' end with phosphorus 32, using a terminal transferase. The sequences of the oligonucleotides used for the screening were determined from the internal peptide sequences mentioned above. These peptides having been generated by cutting with endolysine C, a lysine was again added in first position in order to allow the production of oligonucleotides with the least degeneration. In fact, this amino acid which can only be coded by two codons, is part of the amino acids whose code is least degenerate and as a consequence is quite suitable for the production of oligonucleotides from peptide sequences.

The sequences of oligonucleotides used for the screening of the eucalyptus cDNA library derived from the underlined amino acids (I-inosine) are indicated hereafter:

```
peptide 8 (a)      Lys-Asn-Trp-Cys-Tyr-Gly-Lys
oligonucleotide 8  AA(A/G)AA(C/T)TGGTA(C/T)TG(C/T)TA(T/C)GG
                   IAA peptide 13         Lys-Gly-Cys-Asp-Gly-Val-Val-His-Thr-Ala-
                   Ser-Pro-Val-Thr-Asp-Asp
oligonucleotide 13 AA(G/A)GGITG(C/T)GA(C/T)GGIGTIGTICA peptide 17         Lys-Leu-Arg-Asp-Leu-Gly-Leu-Glu-Phe-Thr
                   Pro-Val-Lys
oligonucleotide 17 GA(G/A)TT(C/T)ACICCIGTIAA peptide 18         Lys-Gly-Asp-Leu-Met-Asp-Tyr-Gly-Ser-Leu-
                   Glu-Glu-Ala-Ile-Lys
oligonucleotide 18 AA(G/A)GGIGA(C/T)(C/T)TIATGGA(C/T)TA
                   (C/T)GG
```

The hybridization conditions used for the screening are as follows: the pre-hybridization is carried out for 6 to 7 hours in 5× SSPE, 0.25% skimmed milk powder, 0.05% SDS (sodium dodecyl sulphate) at 42° C. The hybridization is carried out in the same solution, in the presence of 4 oligonucleotides labelled at the 3' end with ddATPα$^{32}$P, for 24 hours at 42° C. At the end of these 24 hours of hybridization, the filters are washed three times for 15 minutes in 2× SSC, 0.1% SDS then put in contact with an autoradiographic film for 24 hours at −80° C. The phages hybridizing with the group of oligonucleotides were purified by two additional screening rounds (plaque purification). Once purified the six positive clones were tested with each of the oligonucleotides taken independently. One phage reacted positively with the 4 oligonucleotides, it was treated in such a manner as to "excise" the recombinant Bluescript plasmid by following the manufacturer's instructions (Stratagène). The restriction map of the insert (coding for CCR) contained in this plasmid is schematized in FIG. 1.

IV Characterisation and identification of the cDNA of CCR

The amino acid sequence (represented by SEQ ID NO 2) derived from the nucleotide sequence (represented by SEQ ID NO 1) codes for a protein of 335 amino acids the molecular weight of which is 36.5 kD and the isoelectric point of which is about 5.8. It is important to emphasize that all the peptide sequences obtained from the purified CCR are found again in the peptide sequence derived from the nucleotide sequence of the cDNA.

Searches for homologies with clones which already exist were carried out using BLAST and FASTA programs in all available protein and nucleic libraries. One significant homology was found with another reductase of the metabolism of phenol compounds, dihydroflavonol reductase (DFR). The identity is about 40% and the similarity close to 20% between the peptide sequence derived from the cDNA of the CCR and the sequences of the various dihydroflavonol reductase itemized in the libraries, which confirms that the identified clone is different from a clone coding for a DFR.

V Production of active recombinant CCR in E. Coli.

In order to proceed further with the identification of the cDNA of CCR, the recombinant protein was produced in E. Coli and its enzymatic activity was researched. The experimental details of this approach are described hereafter.

1—Introduction of the cDNA in expression vector pT7-7.

In order to be able to clone the cDNA in the expression vector pT7-7 (commercially available), under the control of a promoter of T7 polymerase, we had to introduce a NdeI site in the ATG position of the cDNA. This was carried out using a Taq polymerase during a gene amplification reaction by PCR (Polymerase Chain Reaction) between a mutated oligonucleotide and a commercial primer, T7, situated on Blue script downstream from the 3' end of the cDNA. The amplification product obtained is digested by KpnI, this site is then repaired using a klenow fragment of DNA polymerase I before subjecting the fragment to digestion by NdeI, then the fragment obtained containing an NdeI site in the 5' position and a blunt end in the 3' position is inserted using a DNA T4 ligase in the vector pT7-7 which has been opened beforehand by NdeI and SmaI.

The sequence of the mutated oligonucleotide mentioned above is indicated hereafter.

The underlined and italicized bases were modified relative to the initial sequence allowing the creation of a NdeI site (CATATG):

5'GGCAATCCCCATATGCCCGTCGACGC3'

2. Overexpression of CCR in E. Coli BL21

Figure 2:
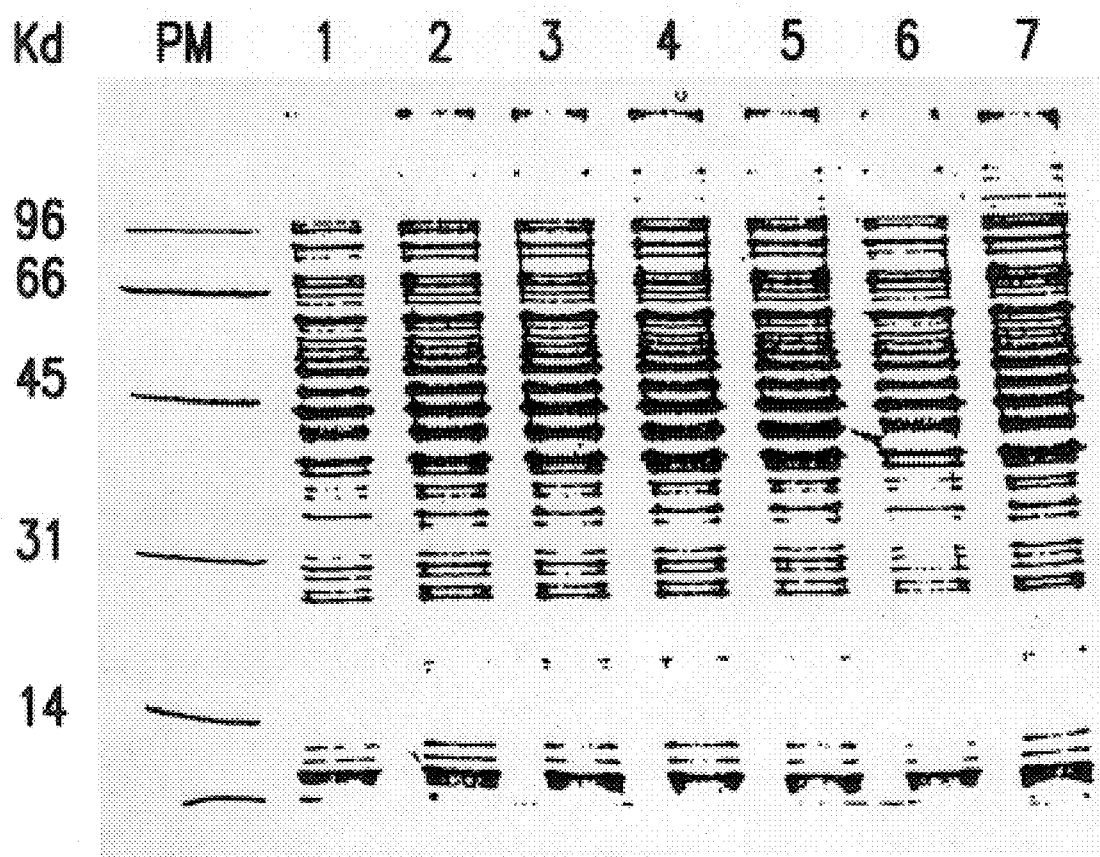

The construction thus obtained is introduced into the strain E. Coli BL21 (commercially available) which carries on its chromosome the gene of the T7 polymerase under the control of promoter lac UV5, a promoter inducible by IPTG. The recombinant culture is cultivated at 37° C. until an OD measured at 1 to 600 nm is obtained, then the production of CCR is induced by the addition of IPTG (0.25% final) into the culture medium. Samples are removed at different times after the induction and the cells are lyzed according to the protocol described by Grima-Pettenati et al. (1993). After centrifuging, the supernatant containing the soluble proteins is used to measure the CCR activity and to show the production of CCR after electrophoresis under denaturing conditions. In FIG. 2, the appearance of a polypeptide of about 38 kD should be noted, the intensity of which increases with post-induction time and which does not exist in the negative controls (strain BL21 containing only the vector pT7-7 without insert). Moreover, the final proof of the identity of the CCR clone is provided by measurement of the CCR activity (about 7 nKat/ml of culture after 3 hours of induction at 37° C.) in the protein extracts originating from BL21 strains containing pT7-7+CCR cDNA only.

Annotations of figures:

FIG. 1: restriction map of cDNA coding for eucalyptus CCR.

FIG. 2: disclosure of an electrophoresis gel with Coomassie blue under denaturing conditions (SDS-PAGE) of total protein extracts of E. Coli BL21 containing the vector pT7-7 without insert (track 6 at time 0 of the induction by IPTG; 7, 3 hours after induction) and the vector pT7-7 containing the cDNA of the CCR (tracks 1, 2, 3, 4, 5, respectively, time 0 of the induction, 30 min, 1, 2, 3 hours after induction), the arrow designates the CCR monomer.

Figure 3:
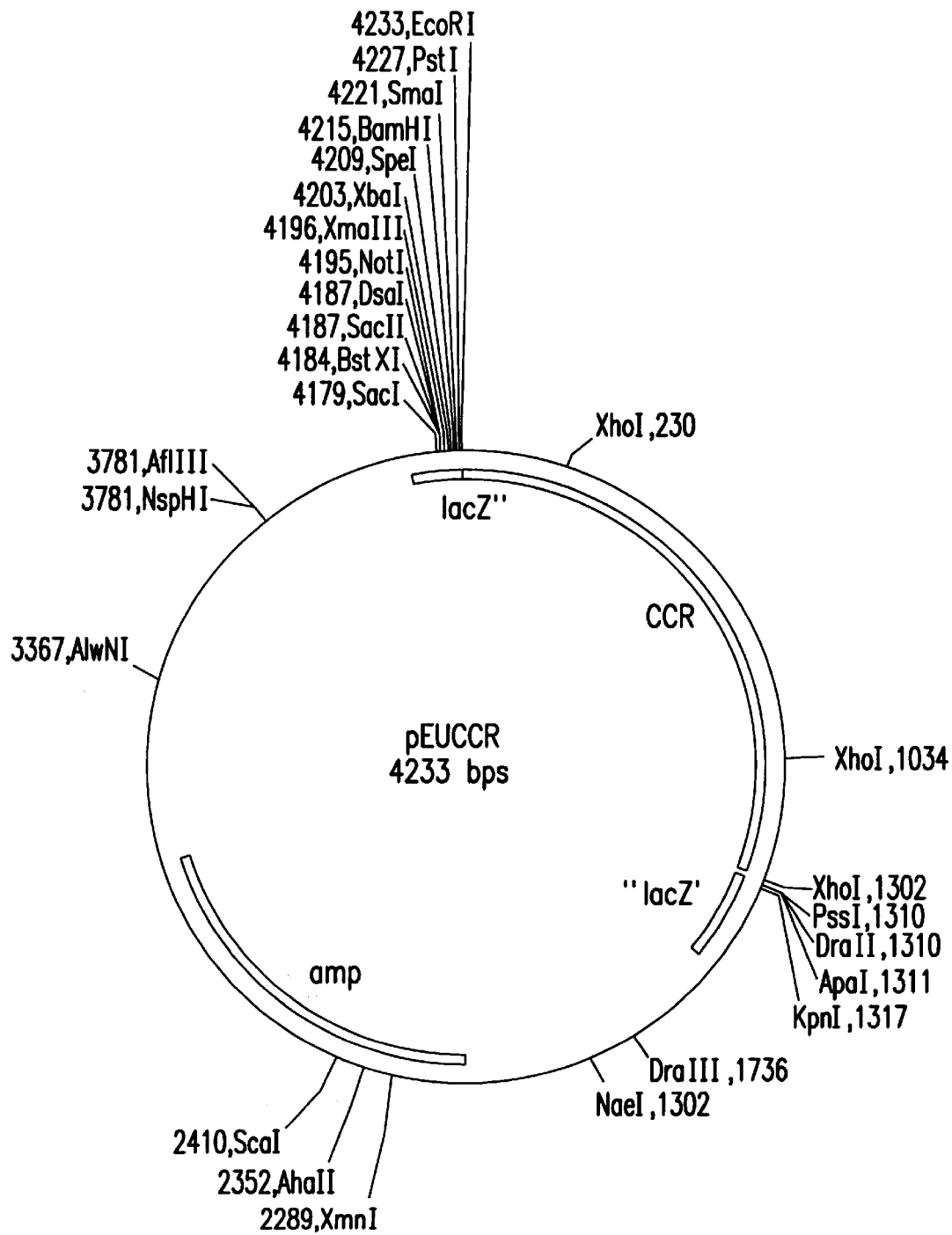

FIG. 3: schematic representation of plasmid pEUCCR containing the sequence represented by SEQ ID NO 1 (and identified by CCR in the plasmid pEUCCR)

Figure 4:
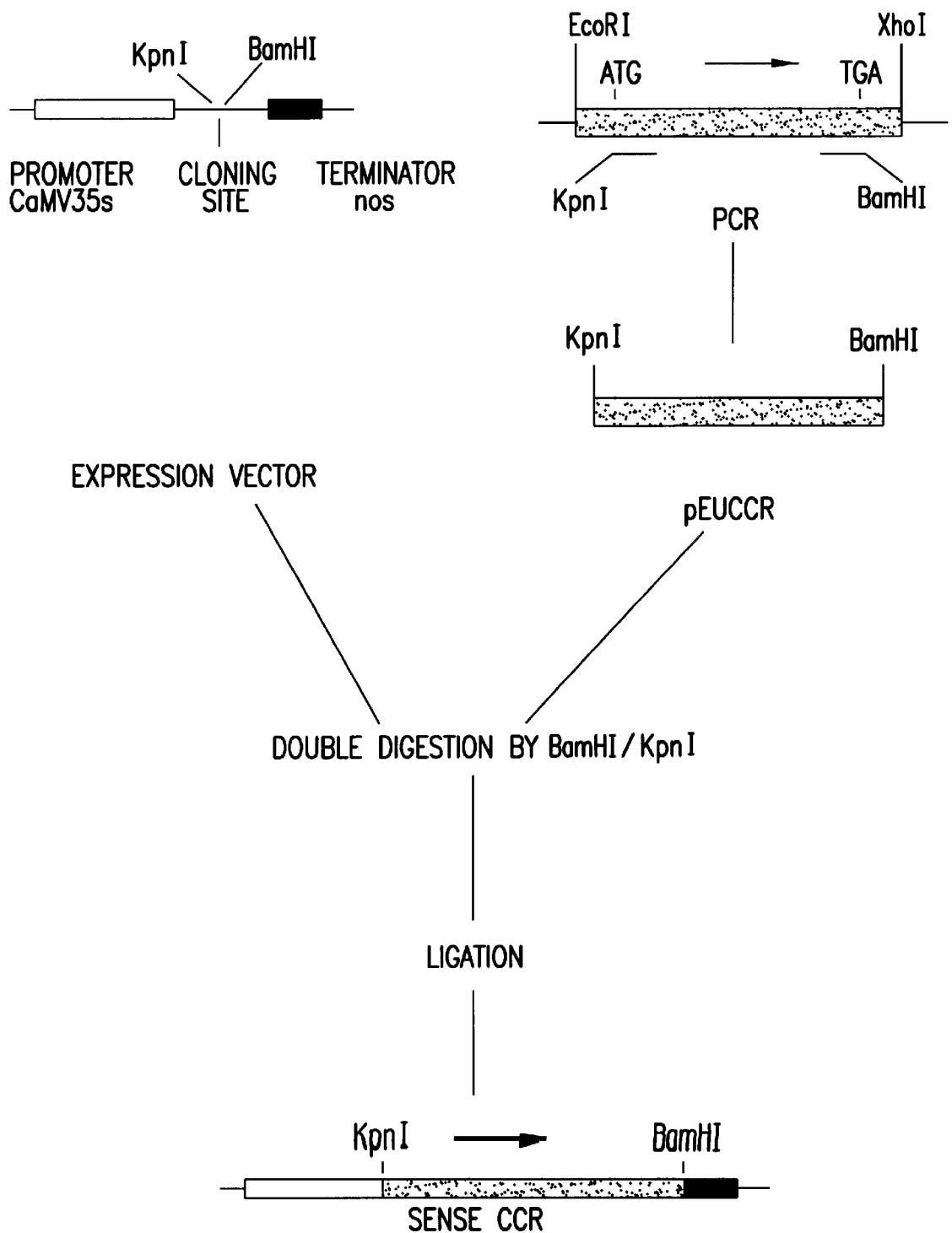

FIG. 4: schematic representation of the construction of a vector containing a DNA sequence coding for eucalyptus CCR according to the invention (or sense CCR vector).

Figure 5:
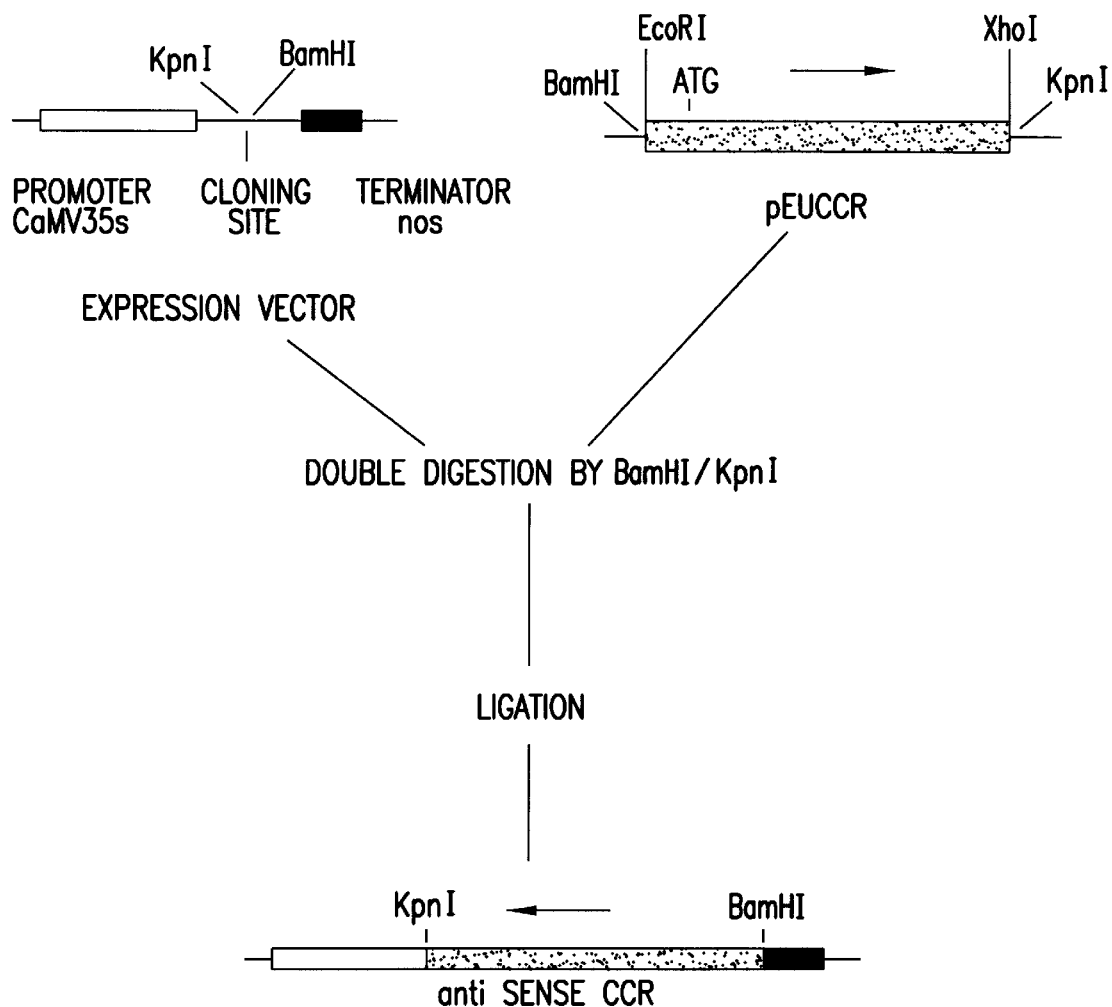

FIG. 5: schematic representation of the construction of a vector containing a DNA sequence coding for an anti sense RNA capable of hybridizing with the mRNA coding for eucalyptus CCR according to the invention (or anti sense CCR vector).

Regarding the DNA source used for the construction of an anti sense (or sense) vector The anti sense RNA is preferably derived from the sequence contained in the clone pEUCCR. This sequence can be obtained in different ways:

1) by cutting the DNA sequence (cDNA) of the CCR contained in pEUCCR with appropriate restriction enzymes,
2) by carrying out a gene amplification (PCR) using oligonucleotides defined so as to synthesis the desired DNA fragment.

The DNA fragment thus obtained is cloned in a plant expression vector downstream from a promoter and upstream from a terminator. The cloning is carried out in such a way that the DNA fragment is inserted in the reverse orientation to the promoter. In this new vector, the strand which was initially the template strand becomes the coding strand and vice versa.

The new vector codes for an RNA the sequence of which is complementary to the sequence of the messenger RNA derived from the sequence contained in pEUCCR.

Therefore the 2 RNAs are complementary not only by their sequence but also by their orientation (5'-3')

As a source of the DNA for the transcription of the anti sense RNA it is practical to use a cDNA clone such as that contained in pEUCCR.

Example of cloning (cf. FIG. 5)

The cDNA of CCR is obtained by a double digestion (BamHI and KpnI) from the vector pEUCCR. The DNA fragment thus released is physically separated from the cloning vector by agarose gel electrophoresis (Bluescript).

The part of the gel containing this DNA fragment is cut out and treated in such a way as to obtain the purified DNA (several methods may be used such as "Low melting Agarose", described in Sambrook et al. mentioned above, the Gene Clean, the kit of which is commercially available).

The fragment carrying the BamHI and KpnI ends is "ligated" with an expression vector of plants digested beforehand by these same enzymes chosen in such a way that the cDNA is inserted in the reverse orientation relative to the 35S promoter. The strand which will be transcribed in the plants will in this case be the non-coding strand.

Example of sense cloning (cf. FIG. 4)

In this case "practical" restriction sites do not exist to carry out translational fusion with the $^{35}$S promoter of the expression vector. New more convenient sites were inserted using the gene amplification technique (PCR). Two oligonucleotides were defined in position 5' and 3' of the cDNAs to which the sequences of sites recognised by KpnI and BamHI were added (NB.: these are the same sites which were used for the anti sense cloning mentioned above, but positioned differently relative to the 5'-3' orientation).

The gene amplification leads to a fragment being obtained containing all the sequence coding for the cDNA flanked by 2 restriction sites. The rest of the procedure is identical to that described for the anti sense construction.

But, in this case, a fusion of the promoter in phase with the ATG of the CCR is carried out which must lead to an overexpression of messenger RNA and therefore of CCR protein.

B) Obtaining the cDNA coding for poplar CCR.

The cDNA was obtained by screening a cDNA library constructed in the λZAPII phage (Stratagène) from messenger extracts of xylem of 2-year-old poplars (*Populus trichocarpa*). The phages were screened using cDNA isolated from *Eucalyptus gunnii* (fragment Xhol of 804 bp of pEUCCR) labelled by random priming with dCTPα$^{32}$P.

The hybridization conditions used for the screening are as follows:
the pre-hybridization is carried out for one night at 68° C. in 6× SSC, 5× Denhardt, 0.5% SDS, 100 μg of salmon sperm DNA. The hybridization is carried out in the same buffer without the addition of the Denhardt reagent, for one night at 60° C. The membranes are then washed twice for 30 minutes in 0.1× SSC, 0.5% SDS at 60° C.

One clone containing the complete cDNA was purified, sub-cloned and sequenced in both directions. The cDNA sequence is that represented by SEQ ID NO 3 and the derived amino acid sequence of the latter is that represented by SEQ ID NO 4.

Comparison between the amino acid sequences of the eucalyptus CCR and that of the poplar show an identity of 83% and a homology of 93% between these two sequences.

C) Obtaining the cDNA coding for fescue CCR.

The cDNA was obtained by screening a cDNA library constructed in the λZAPII phage (Stratagène) from messenger extracts of the leaves of *Fetusca arundinacea*. 500,000 phages were screened using cDNA isolated from *Eucalyptus gunnii* (fragment Xhol of 804 bp of pEUCCR) labelled by random priming with dCTPα$^{32}$P.

The hybridization conditions used for the screening are as follows:
the pre-hybridization is carried out for 6 hours in 5× SSPE, SDS 0.5%, salmon sperm DNA 0.1 mg/ml, Ficoll type 400 1 mg/ml, polyvinylpyrrolidone 1 mg/ml, BSA 1 mg/ml at 60° C. The hybridization is carried out in the same solution in the presence of the probe labelled with dCTPα$^{32}$P, for 16 hours at 60° C. The filters are then washed twice for 15 minutes in 2× SPPE, 0.1% SDS at 60° C. then twice in 0.5× SSPE, 0.1% SDS at 60° C. and finally put in contact with an autoradiographic film for 3 days at –80° C. The phages were purified by 2 or 3 additional screening rounds.

Once purified, 3 clones were analyzed after the plasmid pBluescript had been excised according to the manufacturer's instructions (Stratagène).

The sequencing allowed one clone to be eliminated and the other 2 clones to be shown to be identical and to correspond to the nucleotide sequence represented by SEQ ID NO 5 coding for the fescue CCR as represented by SEQ ID NO 6.

D) Obtaining the cDNA coding for tobacco CCR.

The cDNA was obtained by screening a cDNA library constructed in the λZAPII phage (Stratagène) from messenger extracts of tobacco stems. The phages were screened using cDNA isolated from *Eucalyptus gunnii* (fragment Xhol of 804 bp of pEUCCR) labelled by random priming with dCTPα$^{32}$P.

The hybridization conditions used for the screening are as follows:

the pre-hybridization is carried out in 0.25% Marvel, 5× SSPE, 0.05% SDS at 58° C. The hybridization is carried out in the same buffer, in the presence of 50 ng of a probe labelled with dCTα$^{32}$P, at 58° C. The filters are then washed with 2× SSC/0.1% SDS for 20 minutes at ambient temperature, 2× SSC/0.1% SDS for 20 minutes at 58° C., 1× SSC/0.1% SDS for 15 minutes at 58° C.

The plasmid pBluescript SK⁻ containing the cDNA clone (cloned in the EcoR1 site, using EcoR1 adaptors), was excised in vivo.

The cDNA is represented by SEQ ID NO 7, and the derived amino acid sequence of this cDNA is represented by SEQ ID NO 8.

---

We claim:

1. A method of producing transgenic plants within which the biosynthesis of lignins is regulated either in the sense of an increase, or in the sense of a reduction of the lignin levels produced, relative to the normal lignin levels produced in plants comprising:

transforming plant cells with a recombinant nucleotide sequence comprising one or more coding regions, wherein said coding regions are selected from the group consisting of:

the nucleotide sequence represented by SEQ ID NO 1, coding for a mRNA, said mRNA coding for the CCR of eucalyptus represented by SEQ ID NO 2, the nucleotide sequence represented by SEQ ID NO 3, coding for a mRNA, said mRNA coding for the CCR of poplar represented by SEQ ID NO 4, the nucleotide sequence represented by SEQ ID NO 5, coding for a mRNA, said mRNA coding for the CCR of fescue represented by SEQ ID NO 6, the nucleotide sequence represented by SEQ ID NO 7, coding for a mRNA, said mRNA coding for the CCR of tobacco represented by SEQ ID NO 8, the nucleotide sequence represented by SEQ ID NO 9, coding for a mRNA, said mRNA coding for a protein represented by SEQ ID NO 10, derived from the eucalyptus CCR, and the nucleotide sequence complementary to that represented by SEQ ID NO 1, SEQ ID NO 3, SEQ ID NO 5, SEQ ID NO 7 or SEQ ID NO 9, said complementary sequence coding for an anti sense mRNA capable of hybridizing with the mRNA coded by sequences SEQ ID NO 1, SEQ ID NO 3, SEQ ID NO 5, SEQ ID NO 7 and SEQ ID NO 9, respectively.

2. A DNA sequence comprising:

the nucleotide sequence represented by SEQ ID NO 1, coding for a mRNA, said mRNA coding for the CCR represented by SEQ ID NO 2, or the nucleotide sequence represented by SEQ ID NO 9, coding for a mRNA, said mRNA coding for a protein represented by SEQ ID NO 10 derived from the eucalyptus CCR, or the nucleotide sequence represented by SEQ ID NO 3, coding for a mRNA, said mRNA coding for the CCR represented by SEQ ID NO 4, or the nucleotide sequence represented by SEQ ID NO 5, coding for a mRNA, said mRNA coding for the CCR represented by SEQ ID NO 6, or the nucleotide sequence represented by SEQ ID NO 7, coding for a mRNA, said mRNA coding for the CCR represented by SEQ ID NO 8.

3. A DNA sequence comprising:

the nucleotide sequence complementary to that represented by SEQ ID NO 1, said complementary sequence coding for an anti sense mRNA capable of hybridizing with a mRNA which codes for the CCR represented by SEQ ID NO 2, or the nucleotide sequence complementary to that represented by SEQ ID NO 9, said complementary sequence coding for an anti sense mRNA capable of hybridizing with a mRNA which codes for the CCR represented by SEQ ID NO 10, or the nucleotide sequence complementary to that represented by SEQ ID NO 3, said complementary sequence coding for an anti sense mRNA capable of hybridizing with the mRNA coding for the CCR represented by SEQ ID NO 4, or the nucleotide sequence complementary to that represented by SEQ ID NO 5, said complementary sequence coding for an anti sense mRNA capable of hybridizing with the mRNA coding for the CCR represented by SEQ ID NO 6, or the nucleotide sequence complementary to that represented by SEQ ID NO 7, said complementary sequence coding for an anti sense mRNA capable of hybridizing with the mRNA coding for the CCR represented by SEQ ID NO 8.

4. A mRNA selected from the group consisting of:

the mRNA coded by the DNA sequence represented by SEQ ID NO 1, the mRNA coded by the DNA sequence represented by SEQ ID NO 3, the mRNA coded by the DNA sequence represented by SEQ ID NO 5, the mRNA coded by the DNA sequence represented by SEQ ID NO 7, and the mRNA coded by the DNA sequence represented by SEQ ID NO 9.

5. An anti sense mRNA comprising nucleotides complementary to a mRNA according to claim 4, said anti sense mRNA capable of hybridizing with said mRNA.

6. A recombinant CCR from eucalyptus, poplar, tall fescue or tobacco comprising SEQ ID NO 2, SEQ ID NO 4, SEQ ID NO 6 or SEQ ID NO 8, respectively.

7. A complex formed between an anti sense mRNA according to claim 5, and a CCR mRNA.

8. A recombinant nucleotide sequence comprising at least one DNA sequence according to claim 2, said sequence inserted in a heterologous sequence.

9. A recombinant nucleotide sequence, comprising at least one complementary DNA sequence according to claim 3, inserted in a heterologous sequence.

10. A recombinant nucleotide sequence according to claim 8 comprising the necessary elements to regulate the expression of the nucleotide sequence said necessary elements comprising a promoter or a terminator of transcription and if appropriate, at least one DNA sequence coding for all or part of an enzyme other than CCR which is involved in a stage of the biosynthesis of lignins in plants, in particular the mRNA coding for cinnamyl alcohol dehydrogenase (CAD), or at least one sequence coding for all or part of the anti sense mRNA capable of hybridizing with said mRNA, in particular with the mRNA coding for CAD.

11. A recombinant vector comprising a recombinant nucleotide sequence according to claim 10, integrated in one of its sites of its genome which is non essential for its replication.

12. A process for the regulation of the biosynthesis of lignins in plants, either by reducing, or by increasing the levels of lignin produced, relative to the normal levels of lignins produced in these plants, said process comprising a transformation stage of cells of these plants using a vector containing:

a nucleotide sequence coding for an mRNA, said mRNA coding for a CCR in plants, or a nucleotide sequence complementary to the nucleotide sequence coding for said mRNA, said complementary sequence coding for an anti sense mRNA capable of hybridizing with said mRNA.

13. A process for the reduction of the biosynthesis of lignin in plants and therefore the reduction of the levels of lignins produced relative to the normal levels of lignins produced in plants, comprising the transformation of the genome of said plants, by incorporating:

at least one DNA sequence according to claim 3, and, if appropriate, at least one DNA sequence coding for all or part of an anti sense mRNA capable of hybridizing with a mRNA coding for an enzyme other than CCR, which is implicated in a stage of the biosynthesis of lignins in plants, in particular the mRNA coding for CAD.

14. A process for the reduction of the biosynthesis of lignin in plants and therefore the reduction of the levels of lignins produced relative to the normal levels of lignins produced in plants, comprising the transformation of the genome of said plants, by incorporating:

at least one DNA sequence according to claim 2, and, if appropriate, at least one DNA sequence coding for all or part of an enzyme other than CCR, which is implicated in a stage of the biosynthesis of lignins in plants, in particular a DNA sequence coding for all or part of CAD.

15. A process for increasing the biosynthesis of lignin in plants, and therefore increasing the levels of lignins produced in plants relative to the normal lignin levels produced in plants, comprising the transformation of the genome of these plants, by incorporating:

at least one DNA sequence according to claim 2, and, if appropriate, at least one DNA sequence coding for an enzyme other than CCR, which is implicated in a stage of the biosynthesis of lignins in plants, in particular a DNA sequence coding for CAD.

16. A plant, plant fragment, cell, fruit, seed, or pollen, transformed by incorporation of at least one nucleotide sequence selected from the group consisting of:

the nucleotide sequence represented by SEQ ID NO 1, coding for a mRNA, said mRNA coding for the CCR of eucalyptus represented by SEQ ID NO 2, the nucleotide sequence represented by SEQ ID NO 3, coding for a mRNA, said mRNA coding for the CCR of poplar represented by SEQ ID NO 4, the nucleotide sequence represented by SEQ ID NO 5, coding for a mRNA, said mRNA coding for the CCR of fescue represented by SEQ ID NO 6, the nucleotide sequence represented by SEQ ID NO 7, coding for a mRNA, said mRNA coding for the CCR of tobacco represented by SEQ ID NO 8, the nucleotide sequence represented by SEQ ID NO 9, coding for a mRNA, said mRNA coding for a protein represented by SEQ ID NO 10 derived from the eucalyptus CCR, and the nucleotide sequence complementary to that represented by SEQ ID NO 1, SEQ ID NO 3, SEQ ID NO 5, SEQ ID NO 7 or SEQ ID NO 9, said complementary sequence coding for an anti sense mRNA capable of hybridizing with the mRNA coded by sequences SEQ ID NO 1, SEQ ID NO 3, SEQ ID NO 5, SEQ ID NO 7 and SEQ ID NO 9, respectively.

17. A recombinant polypeptide, comprising SEQ ID NO 2, SEQ ID NO 4, SEQ ID NO 6 or SEQ ID NO 8, obtained by transformation of plant cells by integrating a recombinant nucleotide sequence.

18. The process of claim 12, wherein said nucleotide sequence is selected from the group consisting of:

the nucleotide sequence represented by SEQ ID NO 1, coding for a mRNA, said mRNA coding for the CCR of eucalyptus represented by SEQ ID NO 2, the nucleotide sequence represented by SEQ ID NO 3, coding for a mRNA, said mRNA coding for the CCR of poplar represented by SEQ ID NO 4, the nucleotide sequence represented by SEQ ID NO 5, coding for a mRNA, said mRNA coding for the CCR of fescue represented by SEQ ID NO 6, the nucleotide sequence represented by SEQ ID NO 7, coding for a mRNA, said mRNA coding for the CCR of tobacco represented by SEQ ID NO 8, the nucleotide sequence represented by SEQ ID NO 9, coding for a mRNA, said mRNA coding for a protein represented by SEQ ID NO 10 derived from the eucalyptus CCR, and the nucleotide sequence complementary to that represented by SEQ ID NO 1, SEQ ID NO 3, SEQ ID NO 5, SEQ ID NO 7 or SEQ ID NO 9, said complementary sequence coding for an anti sense mRNA capable of hybridizing with the mRNA coded by sequences SEQ ID NO 1, SEQ ID NO 3, SEQ ID NO 5, SEQ ID NO 7 and SEQ ID NO 9, respectively.

19. A recombinant nucleotide sequence according to claim 9 comprising the necessary elements to regulate the expression of the nucleotide sequence said necessary elements comprising a promoter or a terminator of transcription and if appropriate, at least one DNA sequence coding for all or part of an enzyme other than CCR which is involved in a stage of the biosynthesis of lignins in plants, in particular the mRNA coding for cinnamyl alcohol dehydrogenase (CAD), or at least one sequence coding for all or part of the anti sense mRNA capable of hybridizing with said mRNA, in particular with the mRNA coding for CAD.

20. A recombinant vector comprising a recombinant nucleotide sequence according to claim 19, integrated in one of its sites of its genome which is non essential for its replication.

* * * * *